US006033628A

United States Patent [19]
Kaltenbach et al.

[11] Patent Number: 6,033,628
[45] Date of Patent: Mar. 7, 2000

[54] MINIATURIZED PLANAR COLUMNS FOR USE IN A LIQUID PHASE SEPARATION APPARATUS

[75] Inventors: Patrick Kaltenbach, Bischweier, Germany; Sally A. Swedberg, Los Altos, Calif.; Klaus E. Witt, Keltern; Fritz Bek, Waldbronn, both of Germany; Laurie S. Mittelstadt, Belmont, Calif.

[73] Assignee: Agilent Technologies, Inc., Palo Alto, Calif.

[21] Appl. No.: 08/656,281

[22] PCT Filed: Oct. 16, 1995

[86] PCT No.: PCT/US95/13365

§ 371 Date: Apr. 27, 1998

§ 102(e) Date: Apr. 27, 1998

[87] PCT Pub. No.: WO96/12546

PCT Pub. Date: May 2, 1996

Related U.S. Application Data

[63] Continuation-in-part of application No. 08/482,245, Jun. 7, 1995, Pat. No. 5,658,413, which is a continuation-in-part of application No. 08/326,111, Oct. 19, 1994, Pat. No. 5,500,071.

[51] Int. Cl.[7] .................. G01N 27/26; G01N 27/447; G01N 30/00; G01N 33/50
[52] U.S. Cl. .................. 422/68.1; 422/70; 422/100; 435/287.2; 435/288.5; 204/450; 204/451; 204/453; 204/600; 204/601; 204/604
[58] Field of Search .................. 204/450, 451, 204/452, 453, 454, 455, 600, 601, 602, 603, 604, 605; 422/100, 102, 70, 68.1; 435/287.2, 288.5

[56] References Cited

U.S. PATENT DOCUMENTS

| | | | |
|---|---|---|---|
| 3,770,529 | 11/1973 | Anderson | 164/10 |
| 3,925,166 | 12/1975 | Blume | 435/288.5 |

(List continued on next page.)

FOREIGN PATENT DOCUMENTS

| | | |
|---|---|---|
| 107631 | 5/1984 | European Pat. Off. . |
| 4112 528 A2 | 10/1992 | Germany . |

(List continued on next page.)

OTHER PUBLICATIONS

Stephen C. Jacobson et al, "Fused Quartz Substrates for Microchip Electrophoresis" Analytical Chemistry, vol. 67, No. 13, (Jul. 1, 1995) 2059–2063.

Becker et al. (No month available 1986) "Fabrication of Microstructures with High Aspect Ratios and Great Structural Heights by Synchrotron Radiation Lithography, Galvanoforming, and Plastic Moulding (LIGA Process)" *Microelectric Engineering* 4:35–56.

Beckers et al. (No month available 1988) "Use of a Double–Detector System for the Measurement of Mobilities in Zone Electrophoresis" J. Chromatogr. 452:591–600.

(List continued on next page.)

*Primary Examiner*—Jill Warden
*Assistant Examiner*—John S. Starsiak, Jr.

[57] ABSTRACT

In a method of forming a microchannel and/or microcavity structure by bonding together two elements (1, 2) having opposed plane surfaces of the same or different material, one or both surfaces having open channels and/or cavities, bonding is effected by applying to one or both element surfaces (1, 2) a thin layer (3) of a solution of a material capable of fusing with and having a lower melting point than that of the material or materials of the two element surfaces (1, 2) in a solvent which substantially does not dissolve the element surface material or materials. The solvent is then removed, and the two elements (1, 2) are brought together and heated to a temperature where the dissolved material is caused to melt but not the element surface material or materials.

30 Claims, 18 Drawing Sheets

U.S. PATENT DOCUMENTS

| | | | |
|---|---|---|---|
| 4,668,607 | 5/1987 | Wojcik | 430/281.1 |
| 4,891,120 | 1/1990 | Sethi et al. | 204/600 |
| 4,908,112 | 3/1990 | Pace | 204/601 X |
| 5,037,544 | 8/1991 | Snyder | 210/198.2 |
| 5,126,022 | 6/1992 | Soane et al. | 204/601 |
| 5,132,012 | 7/1992 | Miura et al. | 210/198.2 |
| 5,194,133 | 3/1993 | Clark et al. | 204/608 |
| 5,291,226 | 3/1994 | Schantz et al. | 347/63 |
| 5,305,015 | 4/1994 | Schantz et al. | 347/47 |
| 5,858,195 | 1/1999 | Ramsey | 204/601 |

FOREIGN PATENT DOCUMENTS

| | | |
|---|---|---|
| 60-230-056 | 10/1985 | Japan . |
| 62-087-858 | 4/1987 | Japan . |
| WO94/29400 | 12/1994 | WIPO . |

OTHER PUBLICATIONS

Fan et al. (No month available 1994) "Micromachining of Capillary Electrophoresis Injectors and Separators on Glass Chips and Evaluation of Flow at Capillary Intersections" *Anal. Chem.* 66(1):177–184.

Frazier et al. (No month available 1994) "Development of Micromachined Devices Using Polyimide–Based Processes" *Sensors and Actuators*, A45:47–55.

Harrison et al. (No month available 1993) "Micromachining a Miniaturized Capillary Electrophoresis–Based Chemical Analysis System on a Chip" *Science* 261:895–897.

Harrison et al. (No month available 1993) "Towards Miniaturized Electrophoresis and Chemical Analysis Systems on Silicon: An Alternative to Chemical Sensors" *Sens. Actuators*, B10(2):107–116.

Manz et al. (No month available 1990) "Design of an Open–Tubular Column Liquid Chromatograph Using Silicon Chip Technology" *Sensors and Actuators B (Chemical)* B1(1–6):249–255.

Manz et al. (No month available 1991) "Micromachining of Monocrystalline Silicon and Glass for Chemical Analysis Systems—A Look into Next Century's Technology or Just a Fashionable Craze?" *Trends Anal. Chem.* 10(5):144–149.

Manz et al. (No month available 1993) "Planar Chips Technology for Miniaturization of Separation Systems: A Developing Perspective in Chemical Monitoring" *Adv. Chrom.* 33:1–66.

Pungor et al. (No month available 1983) "Oscillometric Flow Cell for Measurement of Conductivity and Permittivity" *Anal. Chem.* 55:1728–1731.

Pungor et al. (No month available 1992) "Conductance Studies with Use of an Oscillometric Detector" *Electroanalysis* 4:629–634.

Service R. F. (No month available 1995) "The Incredible Shrinking Laboratory" *Science* 268:26–27.

Znotins, T. A. et al. (No month available 1987) "Excimer Lasers: an Emerging Technology in Materials Processing", *Laser Focus Electro Optics* pp. 54–70.

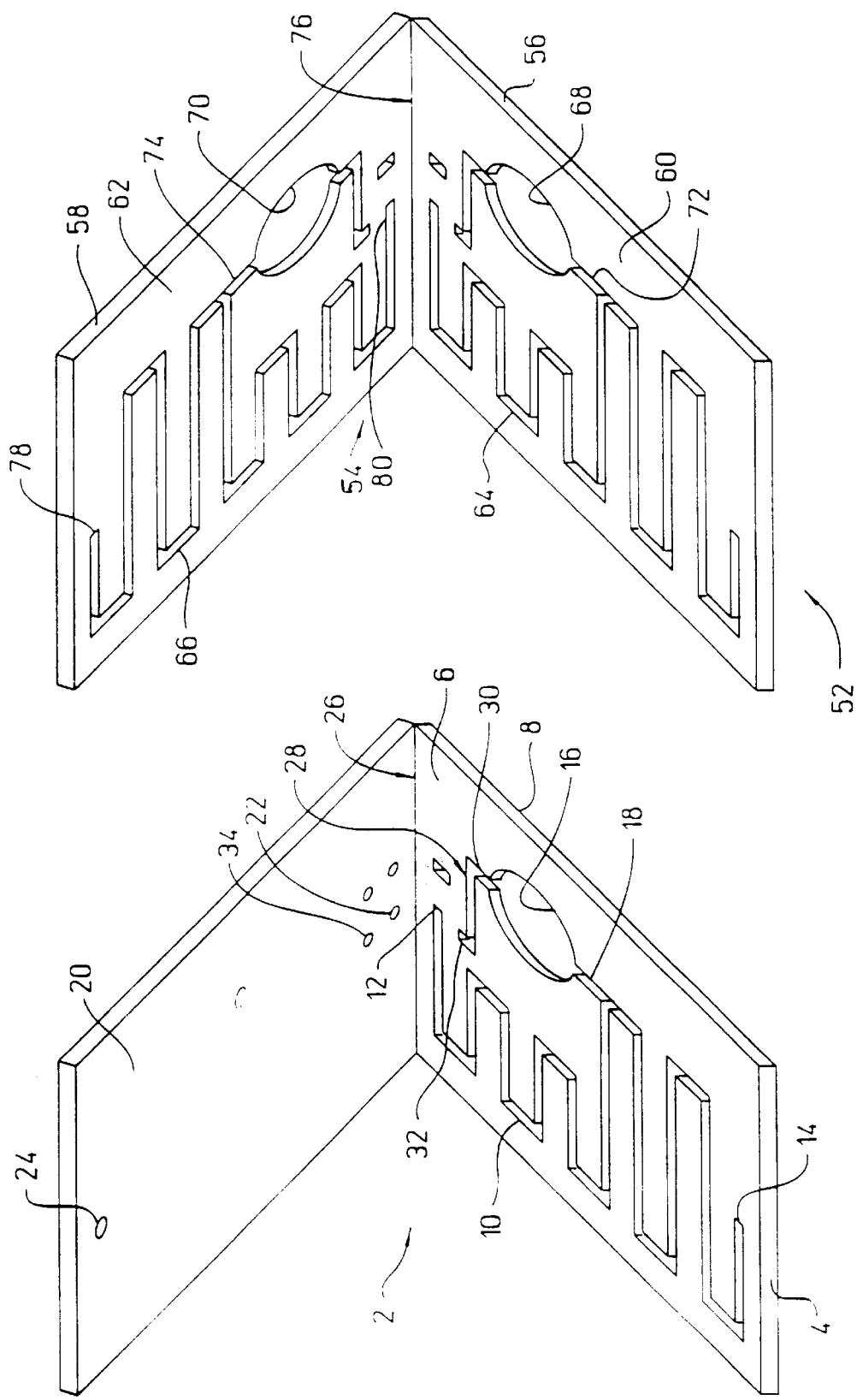

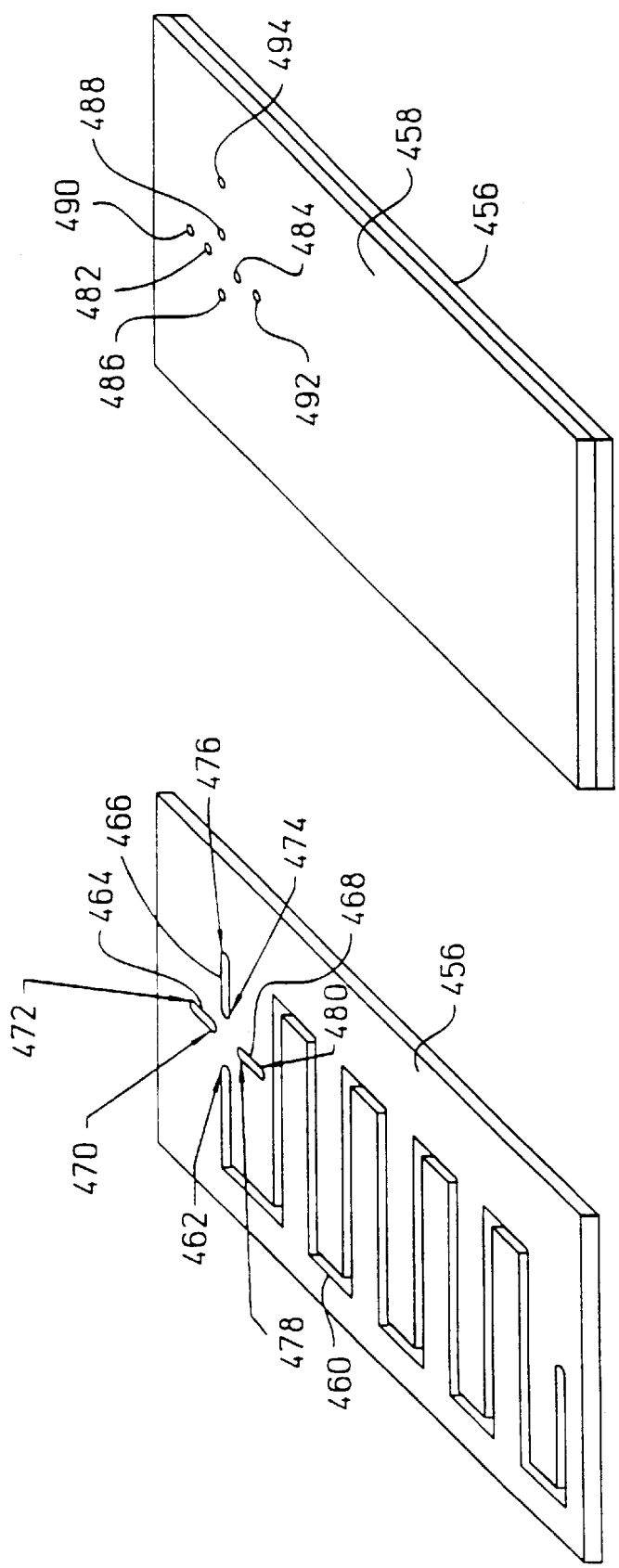

MINIATURIZED PLANAR COLUMNS FOR USE IN A LIQUID PHASE SEPARATION APPARATUS

CROSS-REFERENCE TO RELATED APPLICATIONS

This application is a International 371 of PCT/US95/13395 filed Oct. 16, 1995 and a continuation-in-part of U.S. patent application Ser. No. 08/482,245, filed Jun. 7, 1995 now U.S. Pat. No. 5,658,413; which is a continuation-in-part of U.S. patent application Ser. No. 08/326,111, filed Oct. 19, 1994, now U.S. Pat. No. 5,500,071, from which applications priority is claimed pursuant to 35 U.S.C. §120, and which disclosures are hereby incorporated by reference in their entirety.

TECHNICAL FIELD

The present invention relates generally to miniaturized planar column technology for liquid phase analysis, and more particularly to fabrication of microstructures in novel separation support media using laser ablation techniques. The microstructures find use in any analysis system which may be performed on small and/or macromolecular solutes in the liquid phase and which may employ chromatographic or electrophoretic means of separation.

BACKGROUND OF THE INVENTION

In sample analysis instrumentation, and especially in separation systems such as liquid chromatography and capillary electrophoresis systems, smaller dimensions generally result in improved performance characteristics and at the same time result in reduced production and analysis costs. Miniaturized separation systems provide more effective system design, result in lower overhead, and enable increased speed of analysis, decreased sample and solvent consumption and the possibility of increased detection efficiency.

Accordingly, several approaches towards miniaturization for liquid phase analysis have developed in the art; the conventional approach using drawn fused-silica capillary, and an evolving approach using silicon micromachining.

In conventional miniaturized technology the instrumentation has not been reduced in size; rather, it is the separation compartment size which has been significantly reduced. As an example, micro-column liquid chromatography ($\mu$LC) has been described wherein columns with diameters of 100–200 $\mu$m are employed as compared to prior column diameters of around 4.6 mm.

Another approach towards miniaturization has been the use of capillary electrophoresis (CE), which entails a separation technique carried out in capillaries 25–100 $\mu$m in diameter. CE has been demonstrated to be useful as a method for the separation of a variety of large and small solutes. *J Chromatog.* 218:209 (1981); *Analytical Chemistry* 53:1298 (1981).

A major drawback of the above approaches to miniaturization involves the chemical activity and chemical instability of silicon dioxide ($SiO_2$) substrates, such as silica, quartz or glass, which are commonly used in both CE and $\mu$LC systems. More particularly, silicon dioxide substrates are characterized as high energy surfaces and strongly adsorb many compounds, most notably bases. The use of silicon dioxide materials in separation systems is further restricted due to the chemical instability of those substrates, as the dissolution of $SiO_2$ materials increases in basic conditions (at pHs greater than 7.0).

In order to avoid some of the substantial limitations of conventional $\mu$LC and CE techniques, and in order to enable even greater reduction in separation system sizes, there has been a trend towards providing planarized systems having capillary separation microstructures. In this regard, production of miniaturized separation systems involving fabrication of microstructures in silicon by micromachining or microlithographic techniques has been described. See, e.g.: Fan et al., *Anal. Chem.* 66(1):177–184 (1994); Manz et al., *Adv. in Chrom.* 33:1–66 (1993); Harrison et al., *Sens. Actuators, B* B10(2):107–116 (1993); Manz et al., *Trends Anal. Chem.* 10(5):144–149 (1991); and Manz et al., *Sensors and Actuators B (Chemical)* B1(16):249–255 (1990).

The use of micromachining techniques to fabricate separation systems in silicon provides the practical benefit of enabling mass production of such systems. In this regard, a number of established techniques developed by the microelectronics industry involving micromachining of planar materials, such as silicon, exist and provide a useful and well accepted approach to miniaturization. Examples of the use of such micromachining techniques to produce miniaturized separation devices on silicon or borosilicate glass chips can be found in U.S. Pat. No. 5,194,133 to Clark et al., U.S. Pat. No. 5,132,012 to Miura et al., in U.S. Pat. No. 4,908,112 to Pace, and in U.S. Pat. No. 4,891,120 to Sethi et al.

Although silicon micromachining has been useful in the fabrication of miniaturized systems on a single surface, there are significant disadvantages to the use of this approach in creating the analysis device portion of a miniaturized separation system.

Silicon micromachining is not amenable to producing a high degree of alignment between two etched or machined pieces. This has a negative impact on the symmetry and shape of a separation channel formed by micromachining, which in turn may impact separation efficiency. Also, sealing of micromachined silicon surfaces is generally carried out using adhesives which may be prone to attack by separation conditions imposed by liquid phase analyses. Furthermore, under oxidizing conditions, a silica surface is formed on the silicon chip substrate. Thus, silicon micromachining is fundamentally limited by the chemistry of $SiO_2$. Accordingly, there has remained a need for an improved miniaturized separation system which is able to avoid the inherent shortcomings of conventional miniaturization and silicon micromachining techniques.

SUMMARY OF THE INVENTION

The present invention relates to a miniaturized planar column device for use in a liquid phase separation apparatus.

It is a primary object of the invention to provide a miniaturized column device laser-ablated in a substantially planar substrate, wherein the substrate is of a material selected to avoid the inherent chemical activity and pH instability encountered with silicon and silicon dioxide-based substrates.

It is another object of the invention to provide an on-device reservoir or makeup flow compartment in a miniaturized planar column device, enabling enhanced on-column analysis or detection of components in a liquid sample. It is a related object of the invention to provide a column device for liquid phase analysis having an optional detection means in compact form.

It is yet a further related object of the invention to provide a liquid phase separation apparatus that is capable of performing complex sample handling, separation, and detection methods with reduced technician manipulation or interaction. Thus, the subject invention finds potential application in monitoring and/or analysis of components in industrial chemical, biological, biochemical and medical processes and the like.

The miniaturized planar column devices can be used in a liquid phase separation apparatus which features improved means for liquid handling, including various sample injection means. Thus, a miniaturized column device is provided having a means to interface with a variety of external liquid reservoirs. A particular system design is also provided which allows a variety of injection methods to be readily adapted to the planar structure, such as pressure injection, hydrodynamic injection or electrokinetic injection.

Optional keeper means are described herein and are useful for providing structural support to a miniaturized column device disposed therein. Keeper means further enable the interface of a variety of associated conduit or lightguide means with a column device. Additionally, sample eluate droplet generation and expulsion means are provided to assist in the extraction and collection of a sample eluate from a miniaturized column device. Optional post-column collection devices are also described which cooperate with the liquid phase separation apparatus to collect the sample eluate.

A particular advantage provided by the invention is the use of processes other than silicon micromachining techniques or etching techniques to create miniaturized columns in a wide variety of polymeric and ceramic substrates having desirable attributes for an analysis portion of a separation system. A miniaturized planar column device is formed herein by ablating component microstructures in a substrate using laser radiation. Preferably, a miniaturized column device is formed by providing two substantially planar halves having microstructures laser-ablated therein, which, when the two halves are folded upon each other, define a separation compartment having enhanced symmetry and axial alignment.

Use of laser ablation techniques to form miniaturized devices affords several advantages over prior etching and micromachining techniques used in producing systems in silicon or silicon dioxide materials. The capability of applying rigid computerized control over laser ablation processes allows microstructure formation to be executed with great precision, thereby enabling a heightened degree of alignment in structures formed by component parts. The laser ablation process also avoids problems encountered with microlithographic isotropic etching techniques which may undercut masking during etching, giving rise to asymmetrical structures having curved side walls and flat bases.

Laser ablation further enables the creation of microstructures with greatly reduced component size. Microstructures formed according to the method of the invention may have aspect ratios several orders of magnitude higher than possible using prior etching techniques, thereby providing enhanced separation capability. The use of laser-ablation processes to form microstructures in certain types of substrates, e.g., polymeric substrates, increases ease of fabrication and lowers manufacturing costs as compared with prior approaches such as micromachining devices in silicon. Devices formed using low-cost polymer substrates may also be disposable.

Laser-ablation in planar substrates further allows for the formation of microstructures of almost any geometry or shape. This feature not only enables the formation of complex device configurations, but also allows for integration of sample preparation, sample injection, post-column reaction and detection means in a miniaturized total analysis system.

The compactness of the laser-ablated analysis portion, and the ability to engineer integral functions such as liquid injection, sample handling, detection and sample eluate expulsion into the present devices to provide a liquid phase separation apparatus, also enables the integrated design of system hardware to achieve a greatly reduced system footprint.

The invention thus addresses inherent weaknesses of prior approaches to liquid phase separation device miniaturization, and problems in using silicon micromachining techniques to form miniaturized column devices. Accordingly, the present invention discloses a miniaturized column device for use in a liquid phase separation apparatus that is capable of performing a variety of liquid phase analyses on a wide array of liquid samples.

BRIEF DESCRIPTION OF THE DRAWINGS

FIG. 1 is a plan view of a miniaturized column device which includes an on-device reservoir.

FIG. 2 is a plan view of a miniaturized column device having an on-device reservoir that is formed by the alignment of reservoir means formed on two opposing planar surfaces of a single flexible substrate.

FIG. 16 is a plan view of a miniaturized column device having an alternative sample introduction means ablated in a planar substrate.

FIG. 17 is a plan view of the miniaturized column device of FIG. 16 having a cover plate aligned over the planar substrate.

DETAILED DESCRIPTION OF THE PREFERRED EMBODIMENTS

Figure 3:
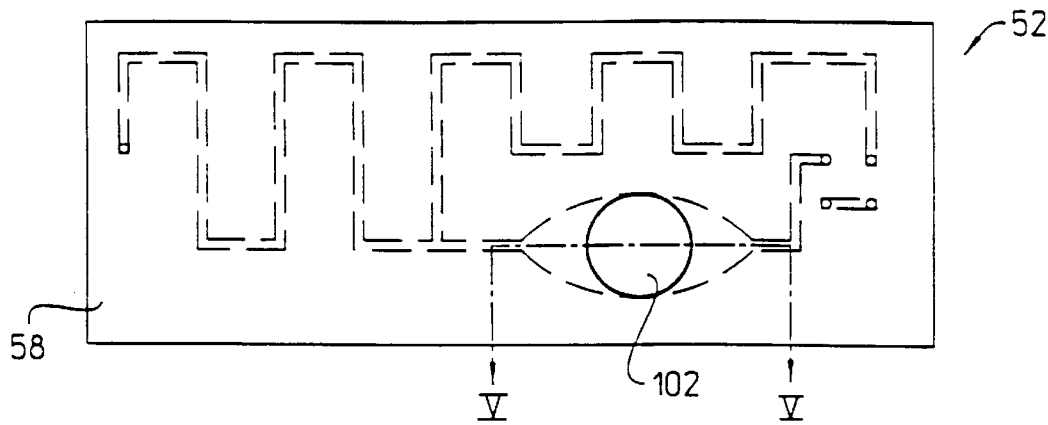
FIG. 3 is a plan view of exterior surface of a miniaturized column device having an optional actuator means disposed over an on-device reservoir compartment.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a detection means" includes two or more such detection means, and the like.

In this specification and in the claims which follow, reference will be made to a number of terms which shall be defined to have the following meanings:

The term "substrate" is used herein to refer to any material which is UV-adsorbing, capable of being laser-ablated and which is not silicon or a silicon dioxide material such as quartz, fused silica or glass (borosilicates). Accordingly, miniaturized column devices are formed herein using suitable substrates, such as laser ablatable polymers (including polyimides and the like) and ceramics (including aluminum oxides and the like). Further, miniaturized column devices are formed herein using composite substrates such as laminates. A "laminate" refers to a composite material formed from several different bonded layers of the same or different materials. One particularly preferred composite substrate comprises a polyimide laminate formed from a first layer of polyimide such as Kapton®, available from DuPont (Wilmington, Del.), that has been co-extruded with a second, thin layer of a thermal adhesive form of polyimide known as KJ®, available from DuPont (Wilmington, Del.). This thermoplastic adhesive layer can be on one or both sides of the first polyimide layer, thereby providing a laminate structure of any desired thickness.

As used herein, the term "detection means" refers to any means, structure or configuration which allows one to interrogate a sample within the separation compartment using analytical detection techniques well known in the art. Thus, a detection means includes one or more apertures or grooves, which communicate with the separation compartment and allow an external detection apparatus or device to be interfaced with the separation compartment to detect an analyte passing through the compartment.

By the arrangement of two detection means opposite each other relative to the separation compartment, a "detection path" is formed, allowing detection of analytes passing through the separation compartment using detection techniques well known in the art.

An "optical detection path" refers to a configuration or arrangement of detection means to form a path whereby electromagnetic radiation is able to travel from an external source to a means for receiving radiation, wherein the radiation traverses the separation compartment and can be influenced by the sample or separated analytes in the sample flowing through the separation compartment. An optical detection path is formed herein by positioning a pair of detection means directly opposite each other relative to the separation compartment. In this configuration, analytes passing through the separation compartment can be detected via transmission of radiation orthogonal to the major axis of the separation compartment (and, accordingly, orthogonal to the direction of electro-osmotic flow in an electrophoretic separation). A variety of external optical detection techniques can be readily interfaced with the separation compartment using an optical detection path including, but not limited to, UV/Vis, Near IR, fluorescence, refractive index (RI) and Raman techniques.

As used herein, a "transparent substance" refers to the ability of the substance to transmit light of different wavelengths, which ability may be measured in a particular substance as the percent of radiation which penetrates a distance of 1 meter. Thus, under the invention, a "transparent sheet" is defined as a sheet of a substance which is transmissive to specific types of radiation or particles of interest. Transparent sheets which are particularly employed in the invention in the context of optical detection configurations are formed from materials such as, but not limited to, quartz, sapphire, diamond and fused silica.

A "detection intersection" refers to a configuration wherein a plurality of detection means that communicate with the separation compartment converge at a particular location in the separation compartment. A number of detection techniques can be simultaneously performed on a sample or separated analyte at the detection intersection. A detection intersection is formed when a plurality of detection paths cross, or when a detection means such as an aperture communicates with the separation compartment at substantially the same point as a detection path. The sample, or a separated analyte, can thus be analyzed using a combination of UV/Vis and fluorescence techniques, optical and electrochemical techniques, optical and electrical techniques, or like combinations to provide highly sensitive detection information. See, e.g., Beckers et at. (1988) *J. Chromatogr.* 452:591–600; and U.S. Pat. No. 4,927,265, to Brownlee.

The use of laser ablation techniques allows for precise alignment of micro-scale components and structures. Such alignment has either been difficult or not possible in prior silicon or glass substrate-based devices. Thus, the term "microalignment" as used herein refers to the precise and accurate alignment of laser-ablated features, including the enhanced alignment of complementary microchannels or microcompartments with each other, inlet and/or outlet ports with microchannels or separation compartments, detection means with microchannels or separation compartments, detection means with other detection means, and the like.

The term "microalignment means" is defined herein to refer to any means for ensuring the precise microalignment of laser-ablated features in a miniaturized column device. Microalignment means can be formed in the column devices either by laser ablation or other methods of fabricating shaped pieces, which methods are well known in the art. Representative microalignment means that can be employed herein include a plurality of coaxially arranged apertures laser-ablated in component parts and/or a plurality of corresponding features in column device substrates, e.g., projections and mating depressions, grooves and mating ridges or the like. The accurate microalignment of component parts can be effected by forming the miniaturized columns in flexible substrates having at least one fold means laser-ablated therein, such that sections of the substrate can be folded to overlie other sections, thereby forming composite micro-scale compartments, aligning features such as apertures or detection means with separation compartments, or forming micro-scale separation compartments from microchannels. Such fold means can be embodied by a row of spaced-apart perforations ablated in a particular substrate, spaced-apart slot-like depressions or apertures ablated so as to extend only part way through the substrate. The perforations or depressions can have circular, diamond, hexagonal or other shapes that promote hinge formation along a predetermined straight line.

The term "liquid phase analysis" is used to refer to any analysis which is carried out on a solute in the liquid phase. Accordingly, "liquid phase analysis" as used herein includes chromatographic separations, electrophoretic separations, and electrochromatographic separations.

"Chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly, electrophoretic separations include separations performed in columns packed with gels (such as polyacrylamide, agarose and combinations thereof) as well as separations performed in solution.

"Electrochromatographic" separations refer to separations effected using a combination of electrophoretic and chromatographic techniques. Exemplary electrochromatographic separations include packed column separations using electromotive force (Knox et al. (1987) *Chromatographia* 24:135; Knox et al. (1989) *J. Liq. Chromatogr* 12:2435; Knox et al. (1991) *Chromatographia* 32:317), and micellar electrophoretic separations (Terabe et al. (1985) *Anal. Chem.* 57:834–841).

The term "motive force" is used to refer to any means for inducing movement of a sample along a column in a liquid phase analysis, and includes application of an electric potential across any portion of the column, application of a pressure differential across any portion of the column or any combination thereof The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

"Optional" or "optionally" as used herein means that the subsequently described feature or structure may or may not be present on the miniaturized column device, or that the subsequently described event or circumstance may or may not occur; and that the description includes instances where a particular feature or structure is present and instances where the feature or structure is absent, or instances where the event or circumstance occurs and instances where it does not. For example, the phrase "a column device optionally having microalignment means" intends that microalignment means may or may not be present on the device and that the description includes both circumstances where such means are present and absent.

In general, any substrate which is UV absorbing provides a suitable substrate in which one can laser ablate features. Accordingly, microstructures of selected configurations can be formed by imaging a lithographic mask onto a suitable substrate, such as a polymer or ceramic material, and then laser ablating the substrate with laser light in areas that are unprotected by the lithographic mask.

In laser ablation, short pulses of intense ultraviolet light are absorbed in a thin surface layer of material within about 1 $\mu$m or less of the surface. Preferred pulse energies are greater than about 100 millijoules per square centimeter and pulse durations are shorter than about 1 microsecond. Under these conditions, the intense ultraviolet light photodissociates the chemical bonds in the material. The absorbed ultraviolet energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other ultraviolet light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins, T. A., et al., *Laser Focus Electro Optics*, (1987) pp. 54–70; U.S. Pat. Nos. 5,291,226 and 5,305,015 to Schantz et al.

Accordingly, the invention concerns formation of miniaturized column devices using laser ablation in a suitable substrate. The column devices are also formed using injection molding techniques wherein the original microstructure has been formed by an excimer laser ablation process, or where the original microstructure has been formed using a LIGA process.

Microstructures such as separation compartments, on-device reservoirs, makeup flow compartments, detection means and micro-alignment means can be formed in a planar substrate by excimer laser ablation. A frequency multiplied YAG laser can also be used in place of the excimer laser. In such a case, a complex microstructure pattern useful for practicing the invention can be formed on a suitable polymeric or ceramic substrate by combining a masking process with a laser ablation means, such as in a step-and-repeat process known to those skilled in the art.

A preferred substrate comprises a polyimide material such as those available under the trademarks Kapton® from DuPont (Wilmington, Del.). or Upilex® from Ube Industries, Ltd. (Japan), although the particular substrate selected can comprise any other suitable polymer or ceramic substrate. Polymer materials useful herein include materials selected from the following classes: polyimide. polycarbonate, polyester, polyamide, polyether, polyolefin, or mixtures thereof. Further, the polymer material selected can be produced in long strips on a reel, and, optional sprocket holes along the sides of the material may be provided to accurately and securely transport the substrate through a step-and-repeat process.

The selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), reservoir means and separation channels.

Alternatively, patterns such as the aperture pattern, the reservoir pattern, the separation channel pattern, etc., can be placed side by side on a common mask substrate which is substantially larger than the laser beam. Such patterns are then moved sequentially into the beam. In other production methods, one or more masks can be used to form apertures through the substrate, and another mask and laser energy level (and/or number of laser shots) can be used to define separation channels and reservoirs which are only formed through a portion of the thickness of the substrate. The masking material used in such masks is, preferably, highly reflecting at the laser wavelength, comprising, for example, a multilayer dielectric material or a metal such as aluminum.

The laser ablation system generally includes beam delivery optics, alignment optics, a high precision and high speed mask shuttle system, and a processing chamber including mechanism for handling and positioning the material. Preferably, the laser system uses a projection mask configuration wherein a precision lens interposed between the mask and the substrate projects the excimer laser light onto the substrate in the image of the pattern defined on the mask.

It will be readily apparent to one of ordinary skill in the art that laser ablation can be used to form miniaturized separation channels, makeup flow ducts and reservoirs in a wide variety of geometries. Any geometry which does not include undercutting can be provided using ablation techniques, such as modulation of laser light intensity across the substrate, stepping the beam across the surface or stepping the fluence and number of pulses applied to each location to control corresponding depth. Further, laser-ablated channels or ducts produced according to the methods of the invention are easily fabricated having ratios of channel depth to channel width which are much greater than previously possible using etching techniques such as silicon micromachining. Such aspect ratios can easily exceed unity, and may even reach to 10.

Channels or ducts of a semi-circular cross-section are preferably laser ablated by controlling exposure intensity or by making multiple exposures with the beam being reoriented between each exposure. Accordingly, when a corresponding semi-circular channel is aligned with a channel thus formed, a separation compartment of highly symmetrical circular cross-section is defined which may be desirable for enhanced fluid flow through the separation device.

As a final step in the above laser ablation processes, a cleaning step is performed wherein the laser-ablated portion of the substrate is positioned under a cleaning station. At the cleaning station, debris from the laser ablation are removed according to standard industry practice.

As will be appreciated by those working in the field of liquid phase analysis devices, the above-described laser ablation methods can be used to produce a wide variety of miniaturized devices.

One such device is represented in FIG. 1 where a particular embodiment of a miniaturized column device is generally indicated at 2. The miniaturized column 2 is formed in a selected substrate 4 using laser ablation techniques. The substrate 4 generally comprises first and second substantially planar opposing surfaces indicated at 6 and 8 respectively, and is selected from a material other than silicon which is UV absorbing and, accordingly, laser-ablatable.

The miniaturized column device 2 comprises a column structure ablated on a chip, which, in the practice of the invention, may be formed from the plastic polyimide. The use of this particular substrate is preferred as, based on considerable experience with the shortcomings of fused silica and research into alternatives thereof, polyimides have proved to be a highly desirable substrate material for the analysis portion of a liquid phase separation system. Specifically, it has been demonstrated that polyimides exhibit low sorptive properties towards proteins, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface which can provide a variety of desirable surface properties, depending on the target analysis. Unlike prior silicon dioxide based systems, these bonds to the polymeric substrate demonstrate pH stability in the basic region (pH 9–10).

Referring still to FIG. 1, the substrate 4 has a microchannel 10 laser-ablated in a first planar surface 6. It will be readily appreciated that although the microchannel 10 has been represented in a generally extended form, microchannels formed in the practice of the invention can be ablated in a large variety of configurations, such as in a straight, serpentine, spiral, or any tortuous path desired. Further, as described above, the microchannel 10 can be formed in a wide variety of channel geometries including semi-circular, rectangular, rhomboid, and the like, and the channels can be formed in a wide range of aspect ratios. It is also noted that a device having a plurality of microchannels laser-ablated thereon falls within the spirit of the invention. The microchannel 10 has an upstream terminus indicated at 12, and a downstream terminus indicated at 14.

The first planar surface 6 further includes an on-device reservoir means 16, formed from a cavity that has been laser-ablated in the first planar surface 6. The cavity can be formed in any geometry and with any aspect ratio, limited only by the overall thickness of the substrate 4, to provide a reservoir means having a desired volume. The reservoir means can be used to provide a makeup flow fluid, a fluid regulation function, or to provide reagents for enhancing detection or separation of liquid sample constituents. The reservoir means 16 is in fluid communication with the microchannel 10 via a fluid conducting means 18, which is formed from a duct laser-ablated in the first planar surface 6.

A cover plate 20 is arranged over the first planar surface 6 and, in combination with the laser-ablated microchannel 10, forms an elongate separation compartment. Further, the cover plate 20, in combination with the reservoir means 16, forms a reservoir compartment, and, likewise, in combination with the fluid conducting means 18, forms a fluid conducting compartment that communicates the reservoir compartment with the separation compartment. The cover plate 20 can be formed from any suitable substrate such as polyimide, where the selection of the substrate is limited only by avoidance of undesirable separation surfaces such as silicon or silicon dioxide materials. Further, the cover plate 20 can be fixably aligned over the first planar surface 6 to form a liquid-tight separation compartment by using pressure sealing techniques, by using external means to urge the pieces together (such as clips, tension springs or associated clamping apparatus), or by using adhesives well known in the art of bonding polymers, ceramics and the like.

In one particular device configuration, the cover plate 20 comprises a discrete component, having a substantially planar surface capable of interfacing closely with the first planar surface 6 of the substrate 4. However, in a preferred device, the substrate and the cover plate are formed in a single, flexible substrate. Referring to FIG. 1, the flexible substrate includes first and second portions, corresponding to the substrate 4 and the cover plate 20, wherein each portion has a substantially planar interior surface. The first and second portions are separated by at least one fold means, generally indicated at 26, such that the portions can be readily folded to overlie each other. The fold means 26 can comprise a row of spaced-apart perforations ablated in the flexible substrate, a row of spaced-apart slot-like depressions or apertures ablated so as to extend only part way through the flexible substrate, or the like. The perforations or depressions can have circular, diamond, hexagonal or other shapes that promote hinge formation along a predetermined straight line.

The miniaturized column device 2 of FIG. 1 can be formed by laser ablating a microchannel 10, a reservoir means 16 and a fluid conducting means 18 in the substrate 4. A separation compartment, reservoir compartment and a fluid conducting compartment are then provided by folding the flexible substrate at the fold means 26 such that the cover plate portion 20 encloses the microchannel, reservoir and fluid conducting means.

In each of the above-described devices, the cover plate 20 can also include a variety of apertures which have been ablated therein. Particularly, a first aperture can be arranged to communicate with the separation compartment (formed by the combination of microchannel 10 and cover plate 20) adjacent the upstream terminus 12 of the microchannel 10 to provide an inlet port 22. The inlet port enables the passage of fluid from an external source into the separation compartment when the cover plate 20 is arranged over the first planar surface 6. A second aperture can likewise be arranged to communicate with the separation compartment adjacent the downstream terminus 14 of the microchannel 10 to form an outlet port 24, enabling passage of fluid from the separation compartment to an external receptacle. Accordingly, a miniaturized column device is formed having a flow path extending from an upstream end of the separation compartment and passing to a downstream end thereof, whereby liquid phase analysis of samples can be carried out by communicating fluids from an associated source (not shown) through the inlet port, passing the fluids through the separation compartment, and allowing the fluids to exit the separation compartment via the outlet port.

A wide variety of liquid phase analysis procedures can be carried out in the subject miniaturized column device using techniques well known in the art. Furthermore, various means for applying a motive force along the length of the separation compartment, such as a pressure differential or electric potential, can be readily interfaced to the column device via the inlet and outlet ports.

In the particular device configuration depicted by FIG. 1, the fluid conducting means 18 enables the fluid communication of the contents from the reservoir means 16 into the separation compartment at a position substantially midway between the upstream and downstream termini, 12 and 14, of the separation microchannel. It is noted that although the fluid conducting means 18 has been depicted in this manner, the fluid conducting means can be arranged to communicate with the separation compartment at any position between, or at, the upstream and downstream termini thereof By communicating the fluid conducting compartment with the middle of the separation compartment, a number of separation or detection enhancing operations may be conducted during the course of a liquid phase analysis. Particularly, the reservoir means 16 can be used to deliver a liquid reagent or dye, e.g., a fluorescent indicator, which is capable of enhancing the detectability of an analyte or sample constituent. Addition of the reagent or dye into the separation compartment during liquid phase analysis allows on-line separation efficiency monitoring to be carried out using detection methods known in the art.

Alternatively, the reservoir means 16 may be used to deliver reagents that are capable of enhancing the efficiency of a particular liquid phase separation. More particularly, a wide variety of organic additives, surfactants, ionic agents, inorganic agents, or the like can be added to the separation compartment after an initial separation has been carried out to increase separation efficiency. A number of variables that affect selectivity and resolution in capillary electrophoresis (CE) are known, including buffer type, agents impacting solution ionic strength, agents that alter dielectric constant or viscosity, and surfactants either above or below their critical micellar concentration (CME). Surfactants below the CMC may associate with the separation compartment surface and hence change the selectivity of the liquid phase separation system. Micellar formation due to the use of surfactants above the CMC may serve as a pseudo packed-column phase in a mechanism of separation known as micellar electrokinetic capillary chromatography (MEKC). Suitable surfactants for MEKC include SDS and CTAB. Additionally, chiral selectors (e.g., cyclodextrins, crown ethers, or the like) can be used to affect enhanced separation of optically active species.

A number of buffer types may be delivered from the reservoir means 16, such as, but not limited to, common organic buffers (e.g., acetate or citrate buffers), inorganic buffers (e.g., phosphate or borate buffers), or Good's buffers (e.g., MES, ACES, MOPS, CAPS, HEPES, and the like). Agents impacting solution ionic strength, such as neutral salts (e.g., NaCl, KCl, or LiCl), can alternatively be delivered from the reservoir means. Agents can also be delivered from the reservoir to affect the dielectric constant of a solution in the separation compartment. Suitable agents include common organic solvents such as, but not limited to, MeOH, EtOH, $CH_3CN$ and isopropyl alcohol. Further, a number of agents can be delivered from the reservoir means 16 to alter the viscosity of the solution passing through the separation compartment, such as methyl cellulose, dextran, polyacrylamide, polyethylene glycol, or polyvinyl alcohol. Agents which can be used in this manner to alter surface wettability include neutral surfactants (TWEEN, BRIJ or alkyloglucosides), zwitterionic surfactants (e.g., CHAPS or CHAPSO), and charged surfactants (SDS or CTAB).

The reservoir means 16 may also be used to optimize a separation by applying increased pressure to the separation compartment after a solute has begun to separate. Specifically, the reservoir means can be employed to deliver a known volume of buffer to the separation compartment at a point after a separation has begun, thereby increasing the pressure exerted on the liquid sample.

In the above devices, optional means may also be provided for communicating a fluid from an external source into the reservoir compartment. Referring still to the device of FIG. 1, a fluid conducting means 28, comprising a duct laser-ablated in the substrate 4 is depicted, having a first end 30 in fluid communication with the reservoir means 16. The fluid conducting means 28 has a second end 32 which is arranged to be in fluid communication with an orifice 34 formed in the cover plate 20 and arranged to communicate with the fluid conducting means when the cover plate is affixed in position over the substrate 4. In one particular device, the orifice 34 comprises an aperture that has been laser-ablated in the cover plate 20. In another particular device, the orifice can be arranged in the cover plate to be in direct fluid communication with the reservoir compartment. However, in each of above-described configurations, the orifice 34 allows interfacing of an external fluid source with the reservoir compartment, whereby externally contained buffers, reagents or like fluids can be introduced into the reservoir compartment for subsequent communication into the separation compartment. The external fluid source can be interfaced with the orifice through associated mechanical valving to provide a divertable fluid connection. This feature allows a variety of injection methods to be used to introduce fluids into the reservoir compartment via the orifice 34, including pressure injection, hydrodynamic injection or electrokinetic injection. The external valving and injection means can communicate with the orifice by butt-coupling thereto; however, any other suitable method of connection known in the art can also be used herein.

Referring now to FIG. 2, a related miniaturized column device is generally indicated at 52. The miniaturized column is formed by providing a support body 54 having first and second component halves indicated at 56 and 58 respectively. The support body may comprise any substantially planar substrate (e.g., a polyimide film) which is both laser ablatable and flexible (so as to enable folding after ablation); however, the particular substrate selected is not considered to be limiting in the invention.

The first and second component halves, 56 and 58, each have substantially planar interior surfaces, indicated at 60 and 62 respectively, wherein miniaturized column features can be ablated. More particularly, a first microchannel pattern 64 is laser-ablated in the first planar interior surface 60 and a second microchannel pattern 66 is laser-ablated in the second planar interior surface 62. The first and second microchannel patterns are ablated in the support body 54 so as to substantially provide the mirror image of each other. In like manner, the column device 52 includes first and second reservoir means, 68 and 70, formed from cavities respectively laser-ablated in the first and second planar surfaces 60 and 62, wherein the cavities are ablated to substantially provide the mirror image of each other. First and second fluid conducting means, indicated at 72 and 74, are formed from ducts laser-ablated in the first and second planar surfaces, wherein the ducts are substantially the mirror image of each other. As described above, the fluid conducting means enable fluid communication between the reservoir means and the microchannels.

The column device 52 is assembled by aligning (such as by folding) the first and second component halves 56 and 58 in facing abutment with each other. The first and second component halves are held in fixable alignment with each other to form liquid-tight separation compartments, reservoir compartments and fluid conducting compartments using pressure sealing techniques, such as the application of tensioned force, or by use of adhesives well known in the art of liquid phase separation devices. As described above, the first and second component halves 56 and 58 are separated by at least one fold means, generally indicated at 76, such that the halves can be folded to overlie each other. In particularly preferred devices, the fold means 76 can comprise a row of spaced-apart perforations ablated in the flexible substrate, spaced-apart slot-like depressions or apertures ablated so as to extend only part way through the flexible substrate, or the like.

The miniaturized column device 52 further includes means for communicating associated external fluid containment means (not shown) with the separation compartment (formed by the alignment of microchannels 64 and 66) to provide a liquid-phase separation device. More particularly, a plurality of apertures can be laser-ablated in the support body 54, wherein the apertures extend from at least one exterior surface of the support body and communicate with at least one microchannel, said apertures permitting the passage of fluid therethrough. More particularly, an inlet port can be laser-ablated in the second component half 58 to communicate with a first end 78 of the microchannel 66. In the same manner, an outlet port can be ablated in the second component half to communicate with a second end 80 of the microchannel 66.

Accordingly, a liquid phase separation device is provided, having a flow path extending from the first end 78 of the microchannel 66 to the second end 80 thereof The flow path is established by communicating fluids from an associated source (not shown) through the inlet port, passing the fluids through the separation compartment formed by the alignment of microchannels 64 and 66, and allowing the fluids to exit the separation compartment via the outlet port. A wide variety of liquid phase analysis procedures can be carried out in the subject miniaturized column device using techniques well known in the art. Furthermore, various means for applying a motive force along the length of the separation compartment, such as a pressure differential or electric potential, can be readily interfaced to the column device via the inlet and outlet ports, or by interfacing with the separation compartment via additional apertures which can be ablated in the support body 54.

Buffers or reagents that have been introduced into the reservoir compartment of the present column devices can be delivered to the separation compartment via fluid conducting means 18 as described above. The fluid flow from the reservoir compartment to the separation compartment may occur via passive diffusion. Optionally, the fluid may be displaced from the reservoir compartment by a motive means such as an actuator or the like. A variety of micropumps and microvalves that will find utility as a motive means herein are well known in the art and have been described, for example, in Manz et al. (1993) *Adv. Chromatogr.* 33:1–66 and references cited therein.

Figure 4:
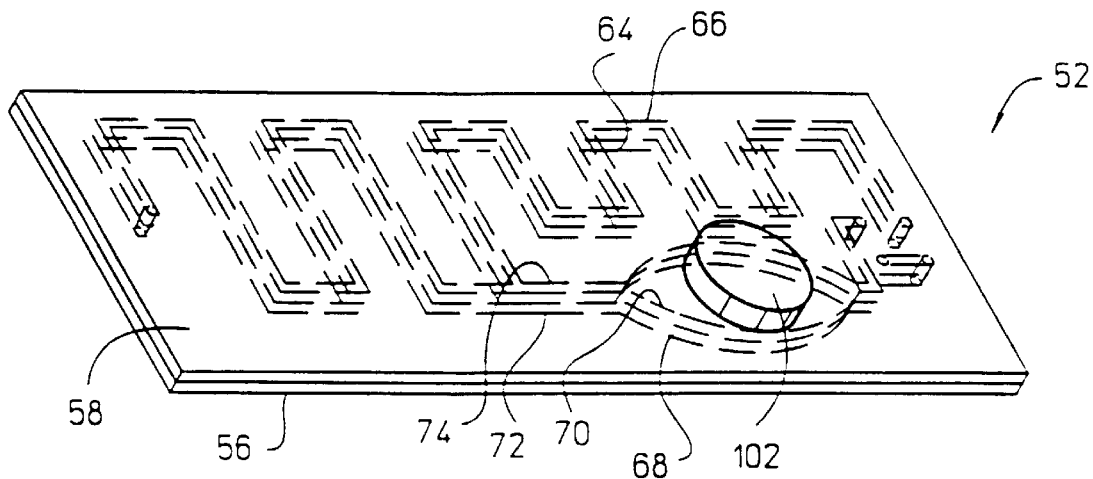
FIG. 4 is a pictorial representation of the miniaturized column device of FIG. 3.
Figure 5:
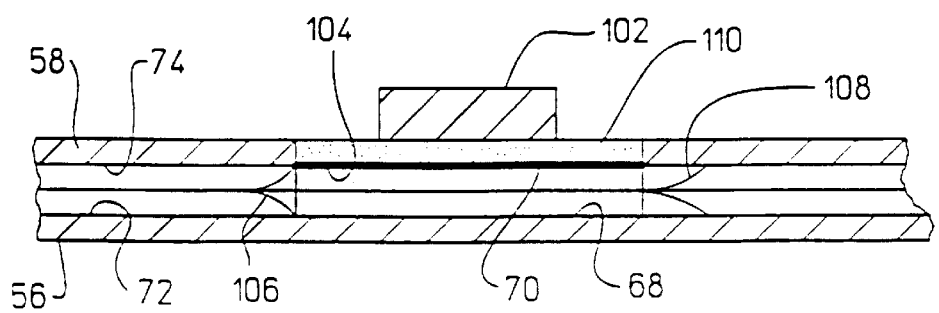
FIG. 5 is a cross-sectional view of the actuator of FIG. 3 taken along lines V—V and showing an optional membrane interposed between the reservoir and actuator means.

Referring to FIGS. 3–5, the miniaturized column device 52 is depicted as including an optional actuator means 102 disposed over the reservoir compartment formed by the alignment of the first and second reservoir means 68 and 70. As best seen in the cross-sectional representation of FIG. 5, the reservoir compartment is optionally covered with thin membrane 104 to form a diaphragm-type pump. A first passive one-way microvalve 106 is optionally integrated into the fluid conducting compartment formed from the alignment of the first and second fluid conducting means 72 and 74 to prevent backflow of displaced fluid into the reservoir compartment, and a second passive one-way microvalve 108 is optionally integrated into reservoir filing means to ensure that the fluid being displaced from the reservoir compartment will travel toward the separation compartment.

Referring still to FIG. 5, an optional gas- or liquid-filled cavity 110 is disposed above the membrane 104. The actuator means 102 can be employed to effect fluid displacement from the reservoir compartment by deflection of the membrane 104. Specifically, the actuator means 102 may act to directly deflect the membrane 104. Accordingly, the actuator means may be a piezoelectric, piston, solenoid or other type of membrane-deflecting device. Alternatively, the actuator means can be a heating means by which the temperature inside cavity 110 is regulated. The heating means can be a resistance-type heating means or any type of suitable heating means known in the art. Upon actuation, the temperature of the heating means increases, thereby heating the contents of cavity 110 and increasing the volume thereof, producing a downward deflection of membrane 104, and displacing fluid from the reservoir compartment, into the fluid conducting means past the valve 106, and into the separation compartment.

Alternatively, heating means 102 may be in thermal contact with the reservoir compartment itself. In this configuration, as the heating means temperature increases, the volume of the fluid in the reservoir compartment increases and is thereby displaced from the reservoir compartment into the separation compartment.

Other examples of pumping mechanisms which may be incorporated into the present devices include those which operate on the principles of ultrasonic-induced transport (Moroney et al. (1991) *Proc MEM S'*91, p. 277) or electrohydrodynamic induced transport (Richter et al. (1991) *Proc MEM S'*91 p. 271). In addition, chemical valves composed of electrically driven polyelectrolyte gels (Osada (1991) *Adv. Materials* 3:107; Osada et al. (1992) *Nature* 355:242) may be used.

The ability to exert rigid computerized control over laser ablation processes enables extremely precise microstructure formation. Such rigid control, in turn, enables the formation of miniaturized columns having features ablated in two substantially planar components, wherein those components can be aligned to define composite separation compartment, reservoir compartments and fluid conducting compartments of enhanced symmetry and axial alignment. Thus, miniaturized column devices are provided wherein laser ablation is used to create two or more component parts which, when folded or aligned with each other, define a single miniaturized column device.

The use of substrates such as polyimides in the construction of the present miniaturized columns allows the possibility of using refractive-index (RI) detection to detect separated analytes of interest passing through the separation compartments. Specifically, the provision of an associated laser diode which emits radiation at a wavelength where polyimide is "transparent" (such as at >500 nm) allows for a detection setup where no additional features need to be provided in the column devices.

Optional detection means can be included in the devices described above. Referring particularly to the device depicted in FIG. 1, one or more detection means can be ablated into the substrate 4 and/or cover plate 20. Preferably, the detection means will be disposed substantially downstream of the upstream terminus 12 of the separation channel 10, to enable detection of separated analytes from the liquid sample. More specifically, an aperture can be ablated through substrate 4 to communicate with the separation channel 10. A corresponding aperture can likewise be formed in cover plate 20, and arranged so that it will be in coaxial alignment with the detection aperture in the substrate when the cover plate is affixed to the substrate to form the separation compartment. Electrodes can be connected to the miniaturized column device via the subject corresponding apertures to detect separated analytes of interest passing through the separation compartment by electrochemical detection techniques. In one particular device configuration, the coaxially aligned apertures form an optical detection path, enabling the optical detection of separated analytes passing through the separation compartment via transmission of radiation orthogonal to the major axis of the separation compartment (and, accordingly, orthogonal to the direction of electro-osmotic flow in an electrophoretic separation).

A wide variety of associated optical detection devices can be interfaced with the miniaturized columns using the optional detection means. Thus, detection of analytes in samples passing through the separation compartment can be readily carried out using UV/Vis, fluorescence, refractive index (RI), Raman and like spectrophotometric techniques.

Further, as will be readily appreciated, the use of optical detection means comprising apertures ablated into the substrate and cover plate provides great control over the effective optical detection pathlength. The resulting detection pathlength will be substantially equal to the combined thickness of the substrate 4 and the cover plate 20.

Figure 6:
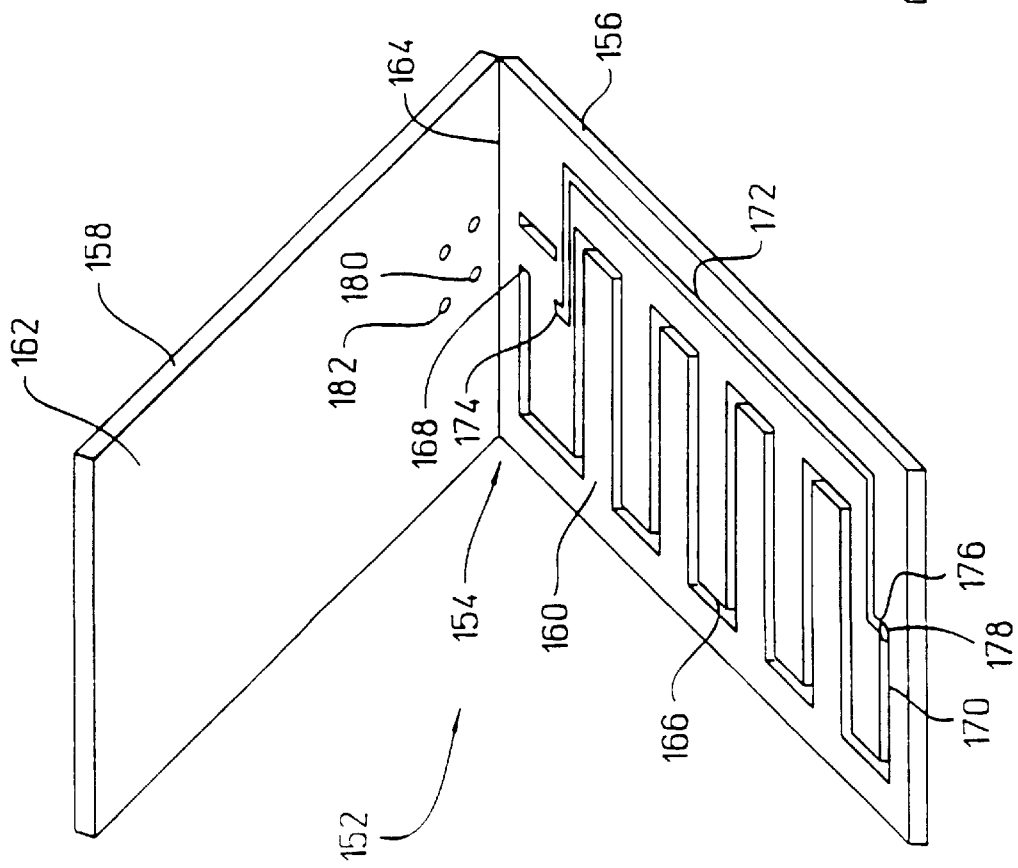
FIG. 6 is a plan view of a miniaturized column device which includes an on-device makeup flow compartment formed in the same planar surface as a separation compartment.

Miniaturized column devices are also provided herein, having an optional makeup flow means capable of supplying a makeup fluid stream to a downstream position on the column to enhance sample collection therefrom. Referring to FIG. 6, a miniaturized column device is generally indicated at 152. The column device is formed in a single, flexible substrate 154 having first and second portions 156 and 158, respectively. The first and second portions have substantially planar interior surfaces, 160 and 162, and are separated by at least one fold means, generally indicated at 164, which enables the portions to be folded to overlie each other as described above.

The column device 152 is formed by laser-ablating a microchannel 166 in the planar surface 160 of the first substrate portion 156. The microchannel extends between an upstream terminus 168 and a downstream terminus 170 to provide a separation channel. A makeup channel 172, comprising a substantially elongate channel having an upstream terminus 174 and a downstream terminus 176 is likewise laser-ablated in the planar surface 160, wherein the makeup channel extends substantially along the length of the separation channel. The downstream terminus 176 of the makeup channel 172 is arranged to communicate with the downstream terminus 170 of the separation microchannel 166. More particularly, the downstream termini of the separation channel and the makeup channel converge at an outlet aperture 178 that has been laser-ablated in the first substrate portion 156.

A separation compartment and a makeup flow compartment are formed when the flexible substrate 154 is folded about the fold means 164 such that the substantially planar interior surface 162 of the second substrate portion 158 overlies the first substrate portion 156. A separation compartment inlet 180 is provided, comprising an aperture laser-ablated in the second substrate portion 158 and arranged to cooperate with the upstream terminus 168 of the separation channel when the interior surfaces of the substrate portions are aligned with each other as described above. Thus, a flow path extending from the upstream terminus of the separation compartment and passing to the downstream terminus is provided, whereby liquid phase analysis of samples can be carried out by communicating fluids from an associated source (not shown) through the inlet 180, passing the fluids through the separation compartment, and allowing the fluids to exit the separation compartment via the outlet aperture 178.

A makeup compartment inlet 182 is also provided, comprising an aperture laser-ablated in the second substrate portion 158 and arranged to cooperate with the upstream terminus 174 of the makeup channel when the interior surfaces of the substrate portions are aligned with each other. Thus, a makeup fluid stream can be passaged from the inlet 182 to converge with an eluate exiting from the separation compartment at the outlet aperture 178.

Figure 7:
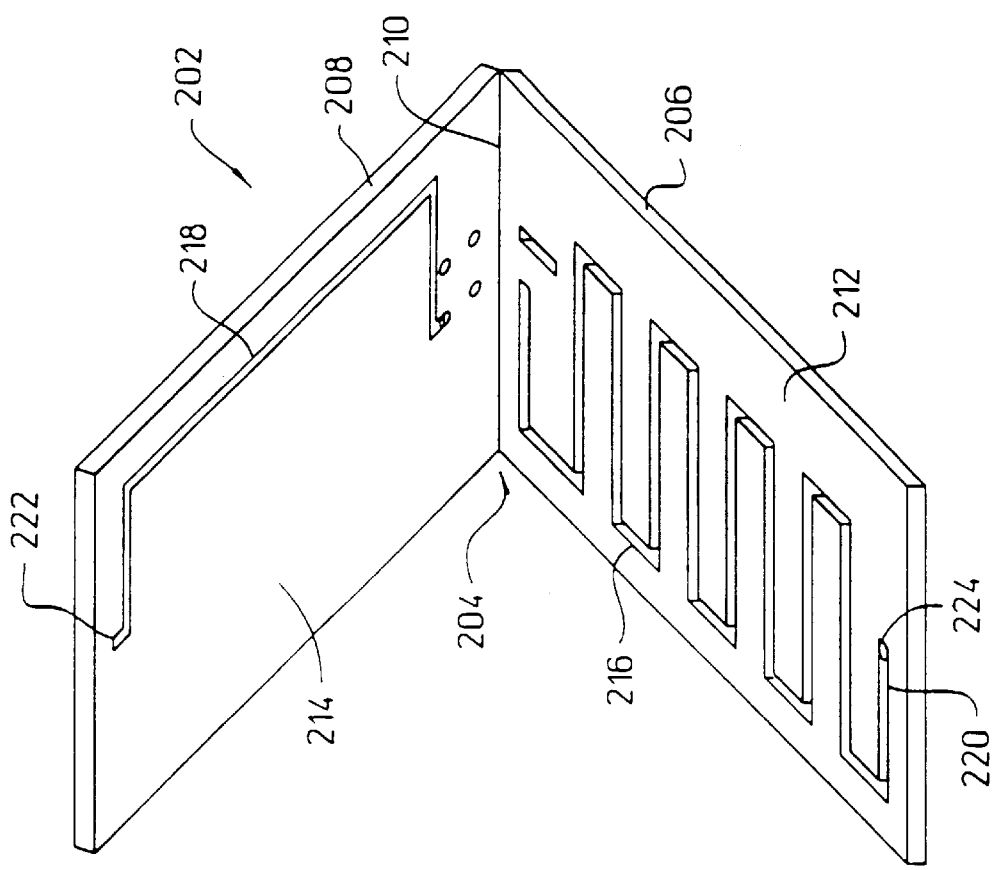
FIG. 7 is a plan view of a miniaturized column device having an on-device makeup flow compartment formed on a different planar surface than a separation compartment.

Referring now to FIG. 7, a related miniaturized column device is generally indicated at 202. The subject device is formed from a single flexible substrate 204 having first and second portions, 206 and 208, wherein the portions are divided by fold means 210. The first and second substrate portions have substantially planar interior surfaces, 212 and 214. A separation channel 216 is laser-ablated in the first planar surface 212 and a makeup channel 218 is laser-ablated in the second planar surface 214. A separation compartment is formed when the substrate 204 is folded about fold means 210 such that the planar surface 214 overlies the separation channel 216. A makeup flow compartment is also formed when the substrate 204 is folded. A downstream terminus 220 of the separation channel 216 and a downstream terminus 222 of the makeup channel 218 are arranged to converge at an outlet port 224, comprising a laser-ablated aperture formed in the substrate portion 206.

A number of optional detection means can be included in the above devices. Referring particularly to the device depicted in FIG. 6, one or more detection means, such as corresponding apertures, can be ablated in each portion of the substrate 154 as has been described. Preferably, the detection means will be disposed substantially downstream of the upstream terminus 168 of the separation channel 166 to enable detection of separated analytes from a liquid sample passing through the separation channel.

Figure 8:
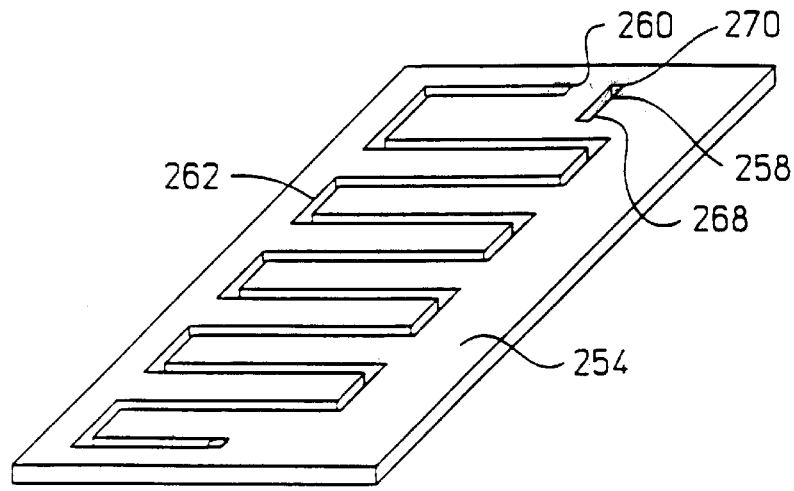
FIG. 8 is a plan view of a miniaturized column device having an optional sample introduction means ablated in a planar substrate.
Figure 9:
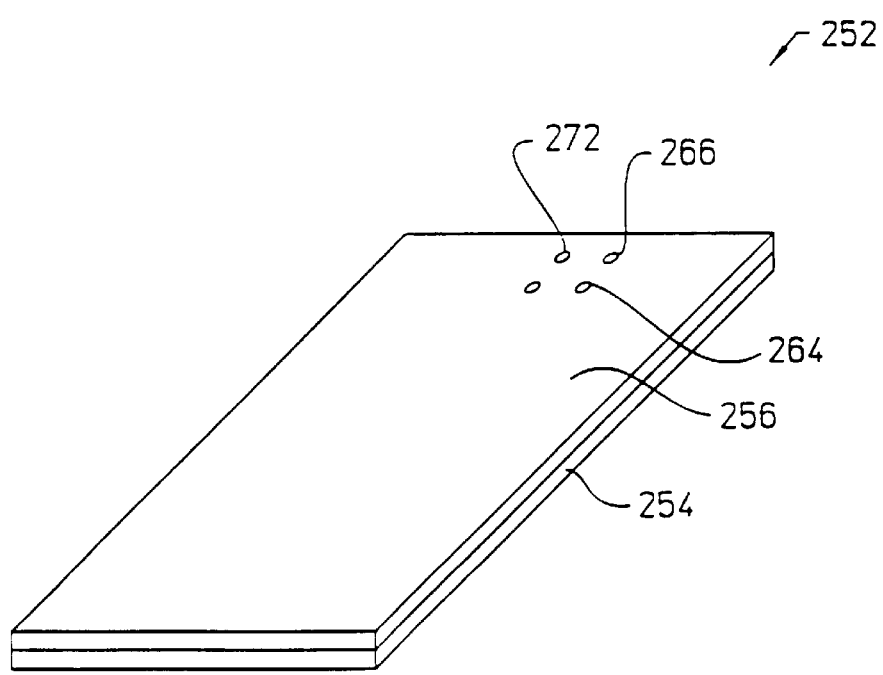
FIG. 9 is a plan view of the miniaturized column device of FIG. 8 having a cover plate aligned over the planar substrate.

Referring now to FIGS. 8 and 9, the above-described miniaturized column devices can include an optional sample introduction means. Particularly, a miniaturized column device 252 is provided having sample introduction means laser-ablated into both a substrate 254 and a cover plate 256. As best seen in FIG. 8, a by-pass channel 258 is laser-ablated in the substrate 254, such that the channel 258 is disposed near an upstream terminus 260 of a separation compartment 262. Two laser-ablated apertures 264 and 266 are formed in the cover plate 256, and are arranged to cooperate with first and second ends (indicated at 268 and 270, respectively) of the by-pass channel 258 when the cover plate is arranged over the substrate. A volumetric sample compartment is formed by aligning the cover plate 256 over the substrate 254 to enclose the by-pass channel 258, whereby a sample being held in an external reservoir can be introduced into the volumetric compartment to form a sample plug of a known volume (defined by the dimensions of the volumetric sample compartment). The sample plug can be delivered to the upstream terminus 260 of the separation compartment 262 via an inlet port 272, comprising an aperture laser-ablated in the cover plate 256. Delivery of the sample plug can be carried out by communicating external mechanical valving with the inlet port and the laser-ablated apertures 264 and 266, and flushing solution through the volumetric sample compartment into the separation compartment.

The ablated by-pass channel 258 and apertures 264 and 266 enable a wide variety of sample introduction techniques to be practiced with the present miniaturized column devices. Further, having a by-pass channel which is not connected to the separation compartment allows a user to flush a sample through the by-pass channel without experiencing sample carry-over or column contamination.

In another embodiment of the invention, a liquid phase separation apparatus is provided, wherein the apparatus is formed from the operative combination of a miniaturized column device as described above and a variety of peripheral elements that enable liquid phase separations to be carried out within the column devices.

Figure 10:
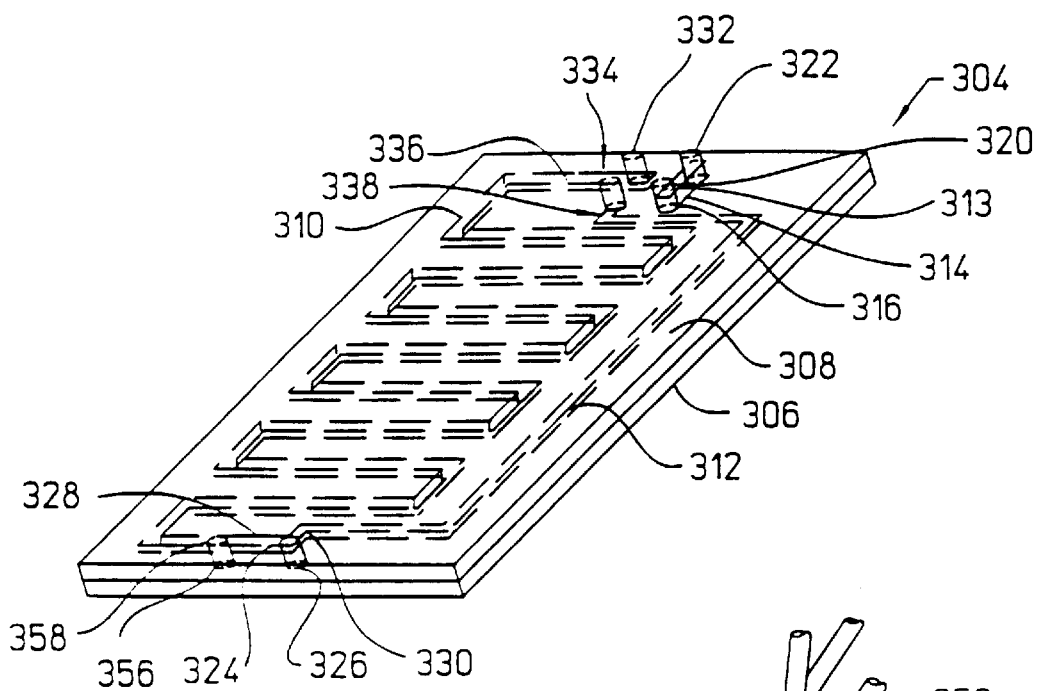
FIG. 10 is a pictorial representation of a miniaturized planar column device and depicts a preferred configuration of a coplanar separation and makeup flow compartments.
Figure 11:
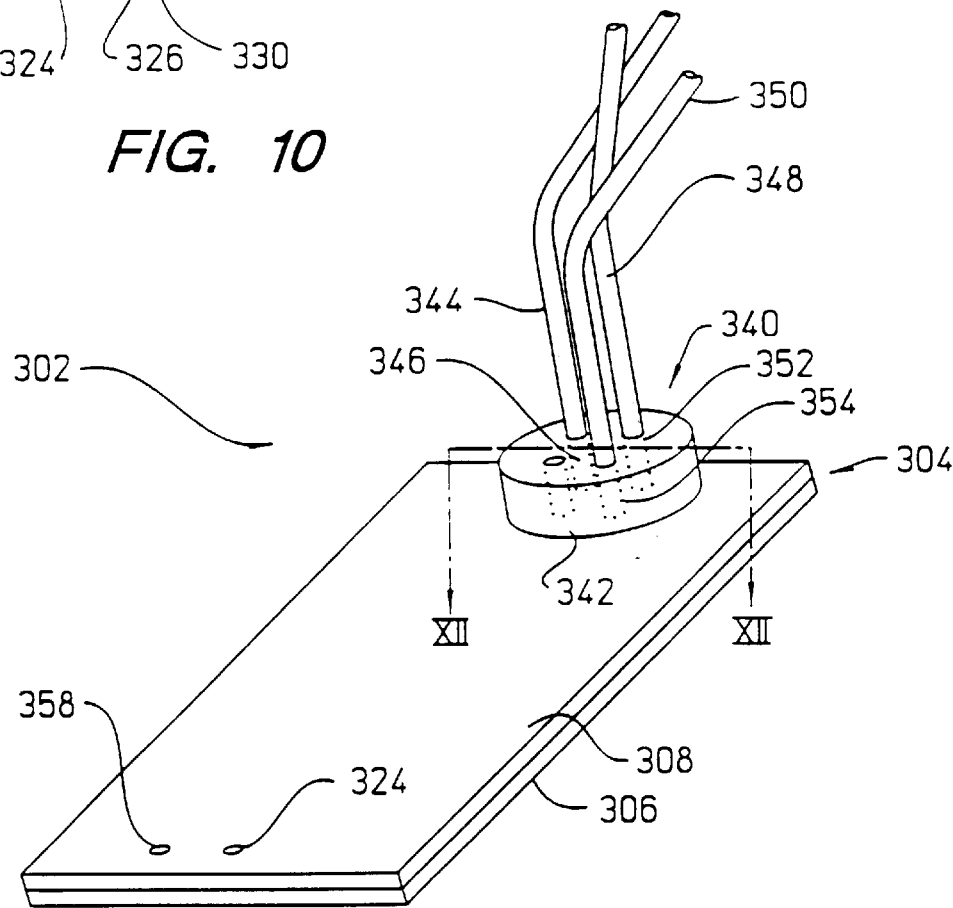
FIG. 11 is a pictorial representation of a liquid phase separation apparatus that includes the device of FIG. 10 and an externally arranged injection means interfaced with the column device.

Referring to FIGS. 10 and 11, a liquid phase separation apparatus is Generally indicated at 302. The apparatus includes a miniaturized column 304, having a substrate portion 306 and a cover plate portion 308. A separation microchannel 310 and an optional makeup flow channel 312 are laser-ablated in the substrate 306 and, in combination with the cover plate 308, form a separation compartment and a makeup flow compartment.

An aperture 324 is arranged in the cover plate 308 to correspond with an outlet port 326. The outlet port comprises an aperture, laser-ablated in the substrate 306, and arranged such that the aperture 324 and the outlet port are positioned in coaxial alignment with each other when the cover plate is fixably aligned over the substrate. The outlet port 326 is also in fluid communication with the downstream terminus 328 of separation microchannel 310 and the downstream terminus 330 of makeup flow channel 312. An inlet port 332, comprising an aperture laser-ablated in the cover plate 308, is arranged to communicate with the upstream terminus 334 of the separation microchannel 310, and allows the formation of a flow path, extending from the upstream terminus 334 of the separation microchannel to the downstream terminus 328, and exiting through the outlet port 326.

A makeup fluid inlet 336, comprising an aperture laser-ablated in the cover plate 308, is arranged to be in fluid communication with the upstream terminus 338 of the makeup flow channel 312 and allows the formation of a makeup fluid flow path extending from the upstream terminus 338 of the makeup flow channel to the downstream terminus 330, and exiting through the outlet port 326.

Figure 12:
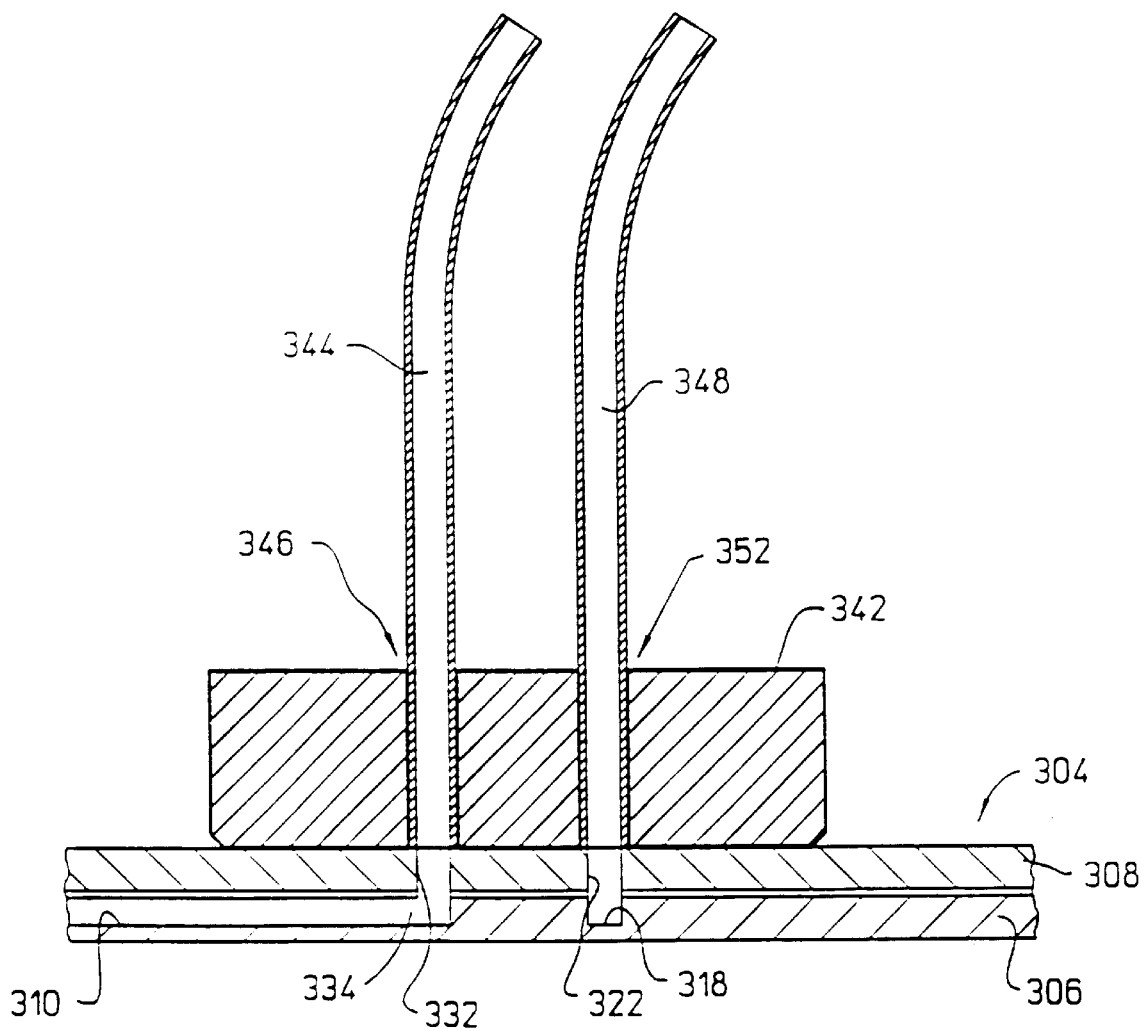
FIG. 12 is a cross-sectional view of the injection means of FIG. 11 taken along lines XII—XII.
Figure 13:
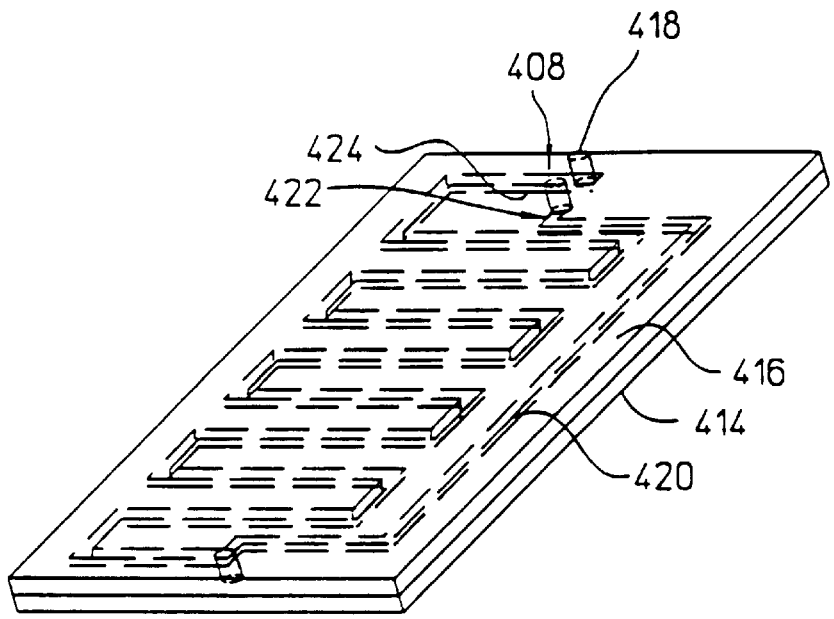
FIG. 13 is a pictorial representation of a miniaturized planar column device similar to the device of FIG. 10.

Referring now to FIGS. 11 and 12, the apparatus 302 further includes an injection means, generally indicated at 340, which allows for the distribution of externally housed liquid samples, buffers, reagents, and makeup flow fluids into the separation compartment and/or the makeup flow compartment. Thus, in one configuration, the sample introduction means can comprise a manifold 342 that closely engages the cover plate 308 of the miniaturized column device 304. and enables the interface of associated conduits and fluid containment means with the inlet port 332 and/or the makeup fluid inlet 336.

The manifold 342 can be coupled to the cover plate 308 to form a liquid-tight interface using pressure sealing techniques known in the art. The manifold and cover plate can be mechanically urged together using clips, tension springs or any suitable clamping means known in the art. The manifold 342 generally includes a plurality of ports that are configured to correspond with the pattern of apertures and inlets present in the cover plate 308. Referring particularly to FIG. 12, a first conduit 344 can be used to interface an associated containment means (not shown) housing a sample to be separated, or a suitable buffer, with the separation channel 310. The conduit 344 is interposed within a port 346 in the manifold 342, and arranged to be in fluid communication with the upstream terminus 334 of the separation channel 310 via the inlet port 332. In this manner, fluids from the associated containment means can be readily delivered to the separation compartment using known injection methods.

The liquid phase separation apparatus 302 can include a column 304 having an optional bypass microchannel 314 laser-ablated in the substrate 306, whereby a volumetric sample compartment is formed in combination with the cover plate 308. The bypass microchannel has first and second termini, 316 and 318, which respectively cooperate with first and second laser-ablated apertures 320 and 322 that are arranged in the cover plate 308 to correspond with the subject termini when the cover plate is aligned over the substrate 306.

Second and third conduit means, 348 and 350, are respectively interposed within ports 352 and 354 in the manifold 342, whereby the conduit means communicate with the bypass microchannel 314 at the first and second termini, 316 and 318, via the first and second laser-ablated apertures 320 and 322. A sample plug having the dimensions of the volumetric sample compartment is thus provided by passing sample through the compartment from an associated containment means using the conduits 348 and 350 to provide a sample flow path to and from the containment means. By manually removing conduits 344, 348 and 350 from the manifold 342, and coupling manifold ports 352 and 346 together by way of a single conduit, a new flow path is provided that passes from the volumetric sample compartment to the upstream terminus 334 of the separation compartment. By coupling the manifold port 354 with a further conduit means that is in fluid communication with a second associated containment means housing a suitable liquid medium, the sample plug can be flushed from the volumetric sample compartment and delivered into the separation compartment by conveying medium from the second containment means to the manifold using known fluid injection methods.

Once the sample has been delivered to the separation compartment, various means for applying a motive force along the length of the separation compartment can be interfaced to the column device 404 using the manifold 406. Particularly, a pressure differential or electric potential can be established along the length of the separation compartment by coupling an external motive means to the upstream terminus of the separation channel via a manifold port.

The liquid phase separation apparatus 302 may further include detection means, disposed in the cover plate 308 and/or the substrate portion 306. The detection means can comprise one or more apertures or features that have been laser-ablated in the cover plate or substrate portion and communicate with the separation compartment at a position adjacent to, or substantially nearby, the downstream terminus 330 of the separation channel 310 to enable the detection of separated analytes. Referring to FIGS. 10 and 11, one particular apparatus includes an aperture 356 that is ablated in the substrate portion 306 and communicates with the separation channel 310 near the downstream terminus 330 thereof. A second aperture 358 is ablated in the cover plate 308, and is arranged to be in coaxial alignment with the aperture 356 when the cover plate is aligned over the substrate as has been described above. The coaxial apertures allow electrodes to be connected to the miniaturized column device 304 via the subject corresponding apertures to detect separated analytes of interest passing through the separation compartment by electrochemical detection techniques. In one particular apparatus, the coaxially aligned apertures form an optical detection path, enabling the optical detection of separated analytes passing through the separation compartment. As will be appreciated by those skilled in the art, a wide variety of associated optical detection devices can be interfaced with the separation compartment via the coaxial apertures, enabling the practice of spectrophotometric techniques such as UV/Vis, fluorescence, refractive index (RI), Raman and the like to detect separated analytes in the liquid sample.

A liquid phase separation apparatus can also be designed to have a manifold means that is movable between a plurality of positions relative to a miniaturized planar column device. Referring now to FIGS. 13, 14 and 15A–C, an apparatus 402 is depicted which includes a miniaturized column device 404 as described herein, and a movable manifold means 406 detachably coupled to the column device 404 and arranged near the upstream terminus 408 of a separation channel 410 that has been laser-ablated in a planar surface 412 of the column substrate 414. A cover plate 416 is arranged over the planar surface 412 of the column substrate, and, in combination with the separation channel 410, forms a separation compartment. An inlet port 418, formed from an aperture laser-ablated in the cover plate 416, communicates with the upstream terminus 408 of the separation channel when the cover plate is positioned over the column substrate.

The column device 404 also includes a makeup flow channel 420 laser-ablated in the planar surface 412. A makeup flow compartment is formed by the combination of the cover plate 416 and the makeup flow microchannel 420. The makeup flow channel has an upstream terminus, 422, which is in fluid communication with a makeup inlet port 424, comprising an aperture laser-ablated in the cover plate 416 and arranged to communicate with the terminus when the cover plate is positioned over the column substrate.

The manifold 406 includes a plurality of ports that are configured to correspond with various apertures and inlets present in the cover plate 416 when the manifold is moved between positions relative to the column device 404. In one particular apparatus, the movable manifold 406 comprises a rotor that is butt-coupled to a stator (not shown) present on the external surface of the miniaturized column device 404, whereby the rotor is capable of moving about the stator between selected positions relative to the column device. When the column device is formed in a polyimide substrate, a ceramic rotor, pressed to the device using tensioned force (to form a liquid-tight seal), is capable of rotating between selected aperture positions on the device due to the friction characteristics of the two materials. Other suitable rotors can be formed in rigid materials such as glass and other non-conductive substrates.

Figure 14:
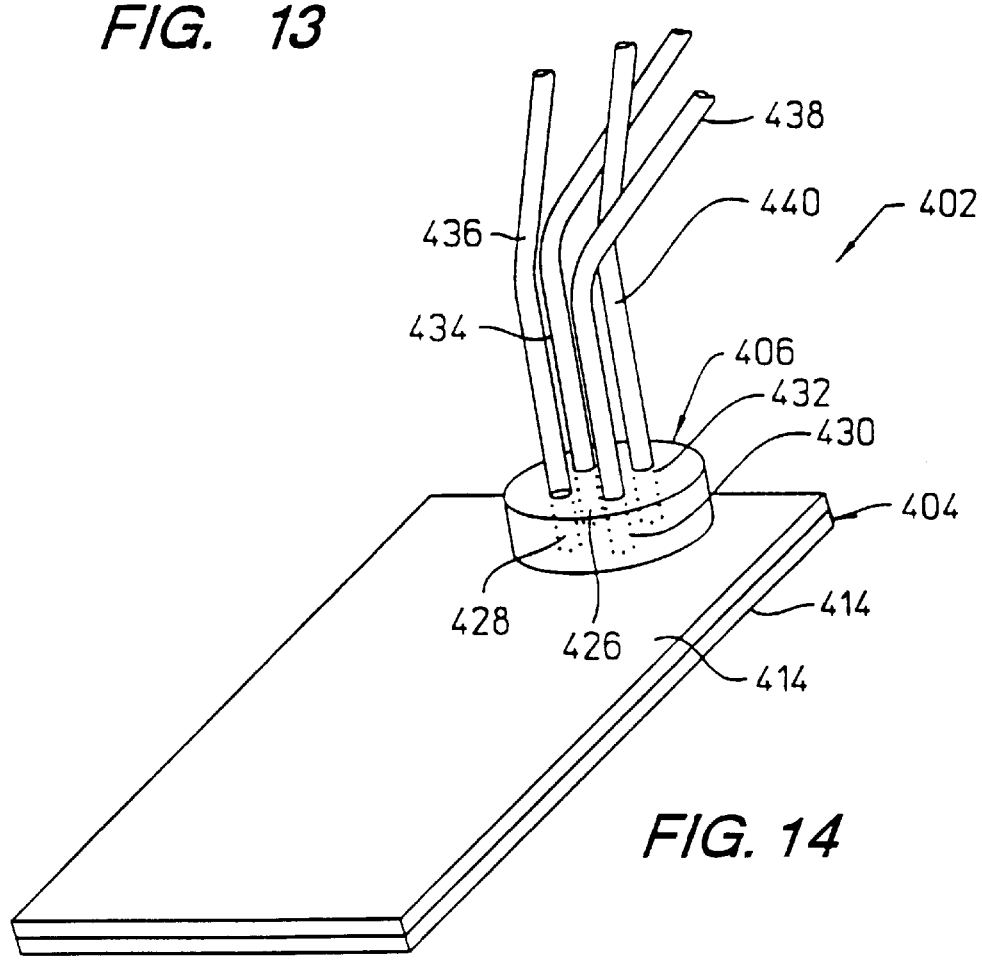
FIG. 14 is a pictorial representation of a liquid phase separation apparatus that includes the device of FIG. 13 and an externally arranged multi-position manifold means interfaced with the column device.
Figure 15A:
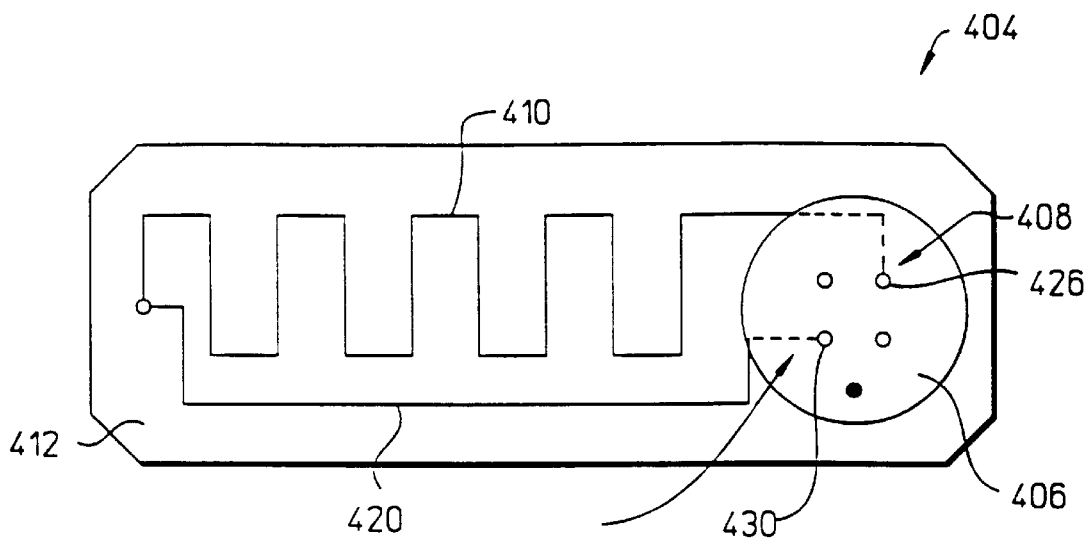
FIG. 15A is a pictorial representation of the apparatus of FIG. 14 with the manifold means arranged in a first position relative to the column device.

Referring particularly to FIG. 14, the manifold 406 includes a first port 426, a second port 428, a third port 430 and a fourth port 432, each port being configured to accept an associated conduit means 434, 436, 438, and 440, respectively. The conduit means are in fluid communication with associated fluid containment means (not shown), such that a fluid sample, reagent or buffer can be communicated to the various ports in the manifold 406 for delivery into the column device 404. Referring now to FIGS. 14 and 15A, when the manifold 406 is in a first position, the first manifold port 426 is in fluid communication with the upstream terminus 408 of the separation channel 410. In this position, a suitable liquid medium, such as an equilabrating buffer or a flush solution, can be delivered into the separation compartment (at the upstream terminus 408) from an associated containment means via the conduit means 434. Further, when the manifold is in the first position, the third manifold port 430 is in fluid communication with the upstream terminus of the makeup flow channel 420. Thus, a suitable liquid medium can be delivered into the makeup flow compartment (at the upstream terminus 422) from the same, or a different associated containment means, via the conduit means 438.

Figure 15B:
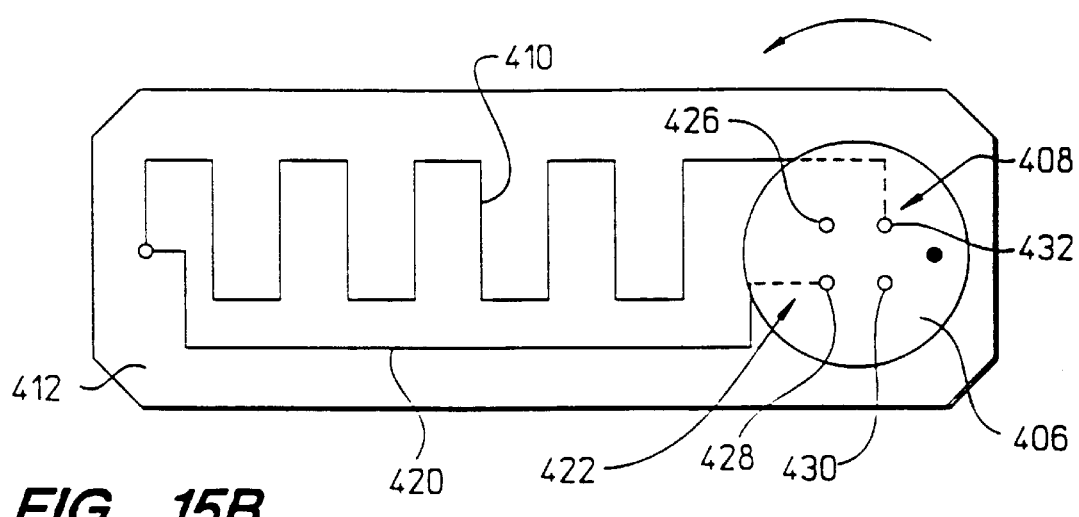
FIG. 15B is a pictorial representation of the apparatus of FIG. 14 with the manifold means arranged in a second position relative to the column device.
Figure 15C:
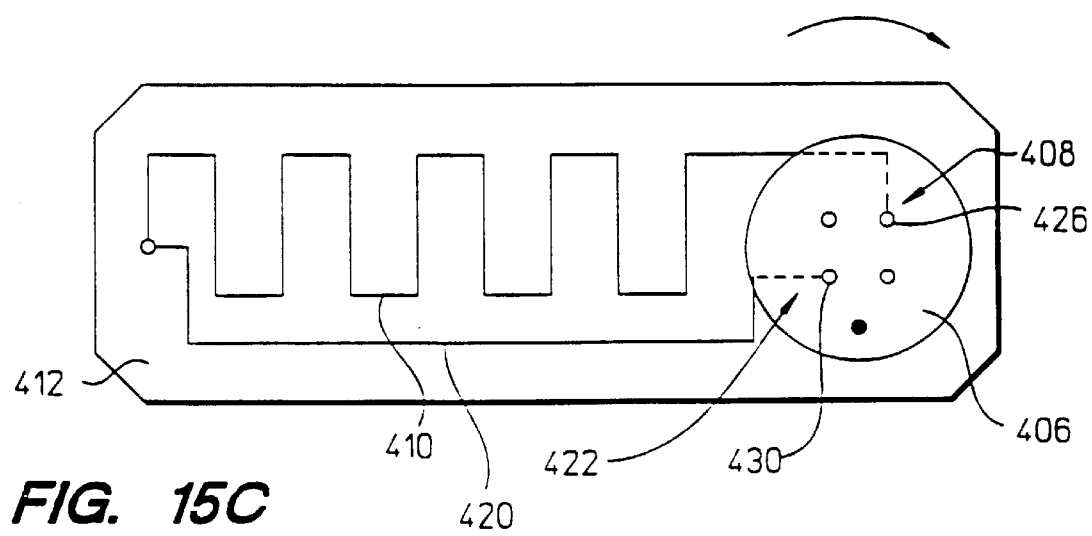
FIG. 15C is a pictorial representation of the apparatus of FIG. 14 with the manifold means returned to a first position relative to the column device.

Referring now to FIGS. 14 and 15B, when the manifold 406 has been rotated counter-clockwise about the stator to a second position relative the column device 404, the fourth manifold port 432 is brought into fluid communication with the upstream terminus 408 of the separation channel 410. Accordingly, a volume or aliquot of liquid sample can be delivered into the separation compartment (at the upstream terminus 408) from an associated sample containment means via the conduit means 440. When the manifold is arranged in the second position, the first and third manifold ports 426 and 430 are moved out of fluid communication with the separation compartment and the makeup fluid compartment such that liquid medium is no longer delivered into those compartments via conduit means 434 and 438.

Further, in the second position, the second manifold port 428 is aligned to be in fluid communication with the upstream terminus 422 of the makeup fluid channel 420, and a liquid reagent, or a heated makeup fluid can be delivered into the makeup flow compartment (at the upstream terminus 422) from an associated sample containment means via the conduit means 436.

Accordingly, a liquid phase separation can be readily carried out using the apparatus 402, wherein the manifold 406 allows switching between a stand-by mode when the manifold is in the first position, and a separation mode when the manifold is in the second position. Alternatively, the above-described two position manifold can be used to alternate between a sample run position, corresponding to the manifold being arranged in the first position, and a sample loading position, corresponding to the manifold being arranged in the second position. The manifold 406 is switched to the second position (e.g., the position depicted in FIG. 15B) to deliver a particular volume of sample into the separation compartment. Once the sample has been delivered, the manifold is rotated clockwise about the stator to return to the first position relative the column device (e.g., the position depicted in FIG. 15C) in order to conduct liquid phase separation of the sample.

Further, as will be appreciated by those skilled in the art, movable, or multi-position manifolds, such as the manifold 406, can be coupled with any of the miniaturized column devices described herein to provide a liquid phase separation apparatus. Thus, such manifolds can be coupled to column devices which include on-device device reservoirs, makeup fluid compartments, volumetric sample compartments and combinations thereof. In this manner, selective and/or temporal delivery of fluids from associated containment means into the various compartments of a miniaturized column is effected using the moveable manifolds described above.

The movable manifold can be configured in a wide variety of shapes, such as, but not limited to, an elongated finger-shaped housing or slide that is capable of either linear or rotational movement between a variety of positions, a circular or oval shaped housing capable of rotational movement between positions, or a semicircular housing that is capable of being rotated between a variety of positions. The manifold can also include any number of ports capable of communicating with an external conduit means, wherein two or more of the ports may also be capable of communicating with each other via lateral interconnecting port means. The configuration of the manifold and the layout of the ports will be generally dictated by the selected configuration of the separation compartment, the associated on-device compartments, the fluid conducting means, and the inlet ports and apertures that communicate with those elements.

A liquid phase separation apparatus may be provided having a movable manifold, wherein the manifold cooperates with an on-device volumetric sample compartment (e.g., a covered bypass channel in fluid communication with inlet and outlet means as described above), to enable the delivery of a sample plug of known volume from the sample compartment to the upstream terminus of a separation compartment. The manifold is detachably coupled to a miniaturized column device, and arranged in a first position such that external conduits disposed within two ports of the manifold enable dynamic fluid communication between the sample compartment (via the inlet and outlet means) and an associated sample containment means. A sample plug, having a volume corresponding to the dimensions of the volumetric sample compartment, is formed by the dynamic flow of sample through the compartment. By moving the manifold to a second position, different ports in the manifold are brought into fluid communication with the volumetric sample compartment inlet and outlet, whereby those ports allow the flow of an externally housed liquid medium through the sample compartment and into the separation compartment via associated conduits and/or lateral ports in the manifold. In this manner, the sample plug disposed within the volumetric sample compartment can be readily delivered to the separation compartment using known liquid injection techniques.

An apparatus may also be provided having a movable manifold that includes an internal volumetric sample compartment. Referring now to FIGS. 16 and 17, a liquid phase separation apparatus is generally indicated at 452. The apparatus includes a miniaturized column device 454, having a substrate portion 456 and a cover plate 458. A separation channel 460 is laser-ablated in a planar surface of the substrate portion 456. The separation channel has an upstream terminus 462 disposed in close proximity to three discrete laser-ablated microchannels, 464, 466, and 468, that are also formed in the substrate portion 456. The microchannel 464 has a first and second terminus, respectively indicated at 470 and 472. Likewise, the microchannel 466 has a first and second terminus, 474 and 476, and the microchannel 468 has a first and second terminus 478 and 480.

A separation compartment is formed by arranging the cover plate 458 over the planar surface of the substrate portion 456. The cover plate includes a plurality of apertures that are arranged to provide fluid communication with the separation compartment and the microchannels 464, 466 and 468 when the cover plate is in place above the substrate. Specifically, laser-ablated apertures 482 and 490, are respectively in fluid communication with the first and second terminus, 470 and 472, of the microchannel 464 to provide a first flow path. Laser-ablated apertures 484 and 492 are respectively in fluid communication with the first and second terminus, 478 and 480, of the microchannel 468 to provide a second flow path. A third flow path is provided by apertures 488 and 494, that are respectively in fluid communication with the first and second terminus, 474 and 476, of the microchannel 466. An aperture, 486, is in fluid communication with the upstream terminus 462 of the separation channel 460.

Figure 18:
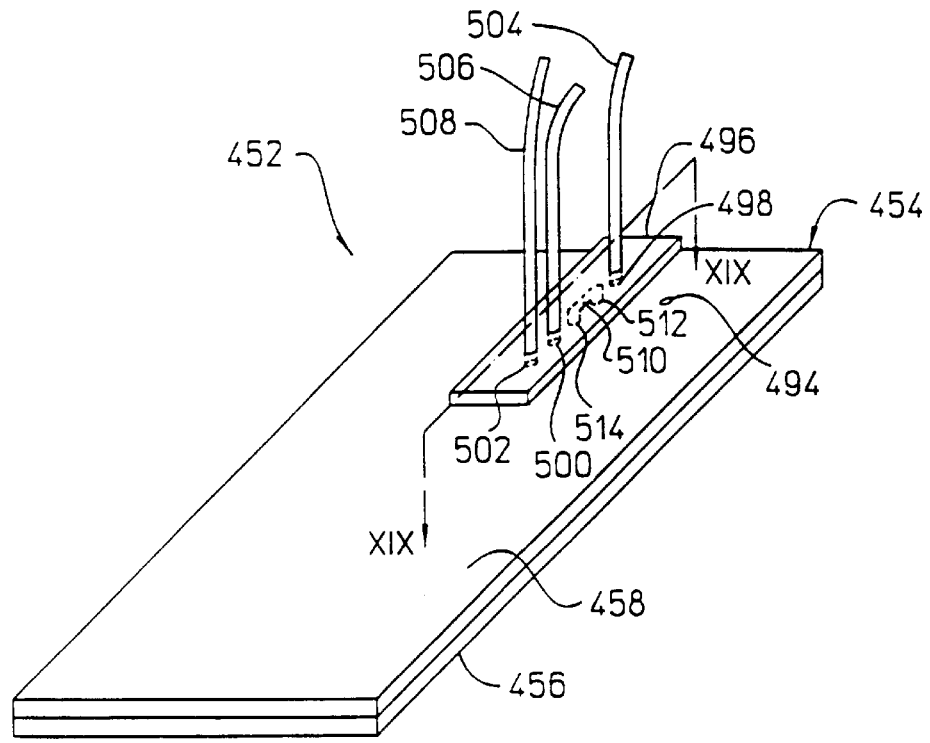
FIG. 18 is a pictorial representation of a liquid phase separation apparatus that includes the device of FIG. 17 and an externally arranged multi-position manifold means interfaced with the column device.
Figure 19:
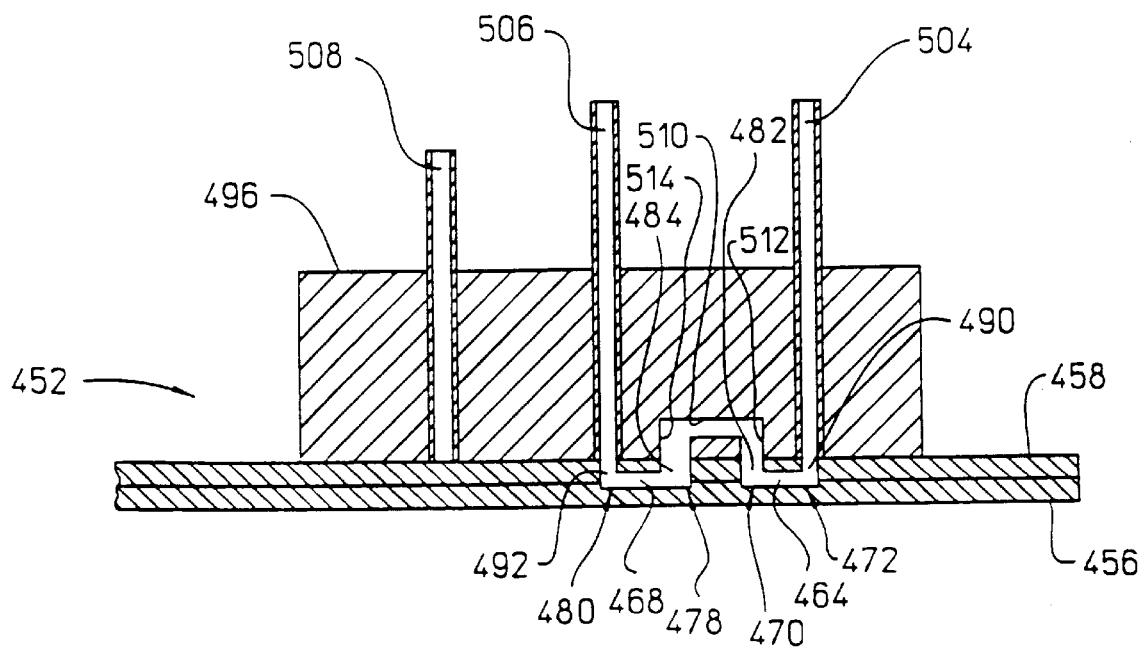
FIG. 19 is a cross-sectional view of the multi-position manifold of FIG. 18 taken along lines XIX—XIX.

Referring now to FIGS. 18 and 19, a movable manifold means 496 is coupled to the cover plate 458 to form a liquid-tight interface using known sealing techniques. Although the manifold means 496 is depicted in an elongated configuration, it is understood that the manifold can be provided in a large variety of suitable configurations as noted above. The manifold means 496 includes first, second and third ports, respectively indicated at 498, 500, and 502, wherein each port can cooperate with an external conduit means, respectively indicated at 504, 506 and 508. The manifold means 496 also includes an internal volumetric sample compartment 510, that comprises a generally U-shaped compartment having a first and second terminus, indicated at 512 and 514, respectively.

In a first position relative to the column device 454, the manifold 496 is arranged such that the manifold port 498 is in fluid communication with the aperture 490, the first terminus 512 of the internal sample compartment is in fluid communication with the aperture 482, the second terminus 514 of the internal sample compartment is in fluid communication with the aperture 484, and the manifold port 500 is in fluid communication with the aperture 492. In this first position, the manifold 496 enables one continuous flow path to be established when the conduit means 504 is communicated with an associated containment means housing a sample. Particularly, the sample is delivered to the microchannel 464 via the conduit means and passed to the volumetric sample compartment 510, continuing through the microchannel 468, and exiting the apparatus via the conduit means 506. Thus, a sample plug is formed within the volumetric sample compartment by the dynamic passage of sample therethrough.

Once a sample plug has been formed in the sample compartment 510, the manifold can be moved to a second position relative to the column device 454 by rotating the manifold counter-clockwise about a pivot (not shown) to bring the manifold port 502 into fluid communication with the aperture 494. Further, the second terminus 514 of the internal sample compartment is brought into fluid communication with the aperture 488, and the first terminus 512 of the internal sample compartment is brought into fluid communication with the aperture 486. In this position, the sample plug can be readily flushed from the volumetric sample compartment and into the separation compartment by passing a liquid medium from an external containment means through the manifold via the conduit means 508, whereby the medium passes through the aperture 494 to flow through the microchannel 466, continuing through the sample compartment 510, and passing through the aperture 486 to the upstream terminus 462 of the separation channel 460.

External hardware can be used to provide mechanical valving for divertable communication of various associated containment means containing, e.g., an electrolyte solution, flush solution or the liquid sample with the column device via the manifold means. Thus, a variety of injection methods can be used, including pressure injection, hydrodynamic injection or electrokinetic injection. The conduit means and any associated valving and injection means can communicate with the separation device through the manifold means, or communicate directly with the separation device by butt-coupling to apertures, however, any other suitable method of connection known in the art can be readily adapted to the invention. Further, it is noted that numerous other sample introduction and fluid interfacing designs can be practiced and still fall within the spirit of the subject invention.

Figure 20:
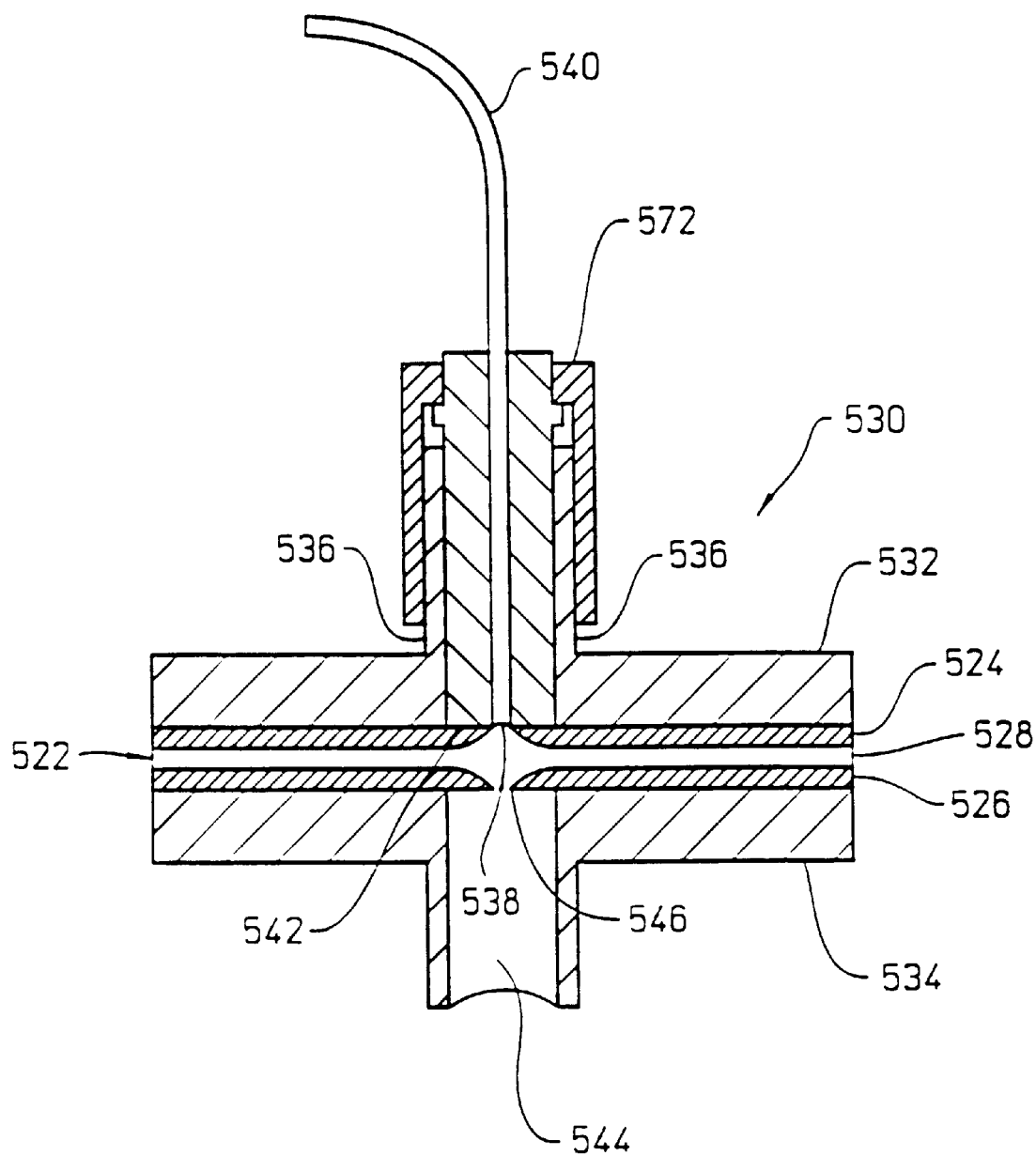
FIG. 20 is a cross-sectional view of a keeper means housing a miniaturized column device and enabling the interface of associated lightguide means with a detection means in the column device.

A liquid phase separation apparatus may also be provided having an associated keeper means that is adapted to receive and provide support to a miniaturized column device. Referring to FIG. 20, a miniaturized column 522 is depicted having first and second component halves 524 and 526. A separation channel 528 is provided by the alignment of corresponding channels that have been laser-ablated in each half to provide the mirror image of each other. The column 522 is supported by a keeper means 530 that generally comprises first and second opposable elements, 532 and 534, that are constructed to closely accept and provide structural support to the miniaturized column.

The keeper means can include optional means for facilitating the coupling of an associated conduit, lightguide or fastener with an aperture, inlet port, outlet port or detection means. Referring still to FIG. 20, the keeper means 530 includes an annular boss 536 that extends from the first opposable element 532. The annular boss is arranged to encircle an area including a detection means 538. The detection means 538 is formed from an aperture that has been laser-ablated in the component half 524 and communicates with the separation compartment 528. An associated lightguide means 540 is readily interfaced with the detection means 538 by the insertion of a distal end 540 thereof into the annular boss. A second annular boss, 544, extends from the second opposable element 534, and is arranged to encircle an area including a second detection means 546. The second detection means 546 is formed from an aperture that has been laser-ablated in the component half 526 and is arranged in coaxial alignment with the first detection means 538 to provide an optical detection path. A further lightguide means can thus be inserted into the second annular boss 544, whereby the contents of the separation compartment can be interrogated using associated optical detection means to detect separated analytes in the sample undergoing liquid phase analysis.

Although the annular bosses have been described herein in conjunction with coupling lightguide means with detection means, it will be appreciated by those skilled in the art that such means can be arranged in a plurality of locations about the keeper means to encircle inlets, outlets and apertures, whereby associated conduit means can be readily coupled to the devices to communicate fluids to and from the miniaturized columns.

Figure 21:
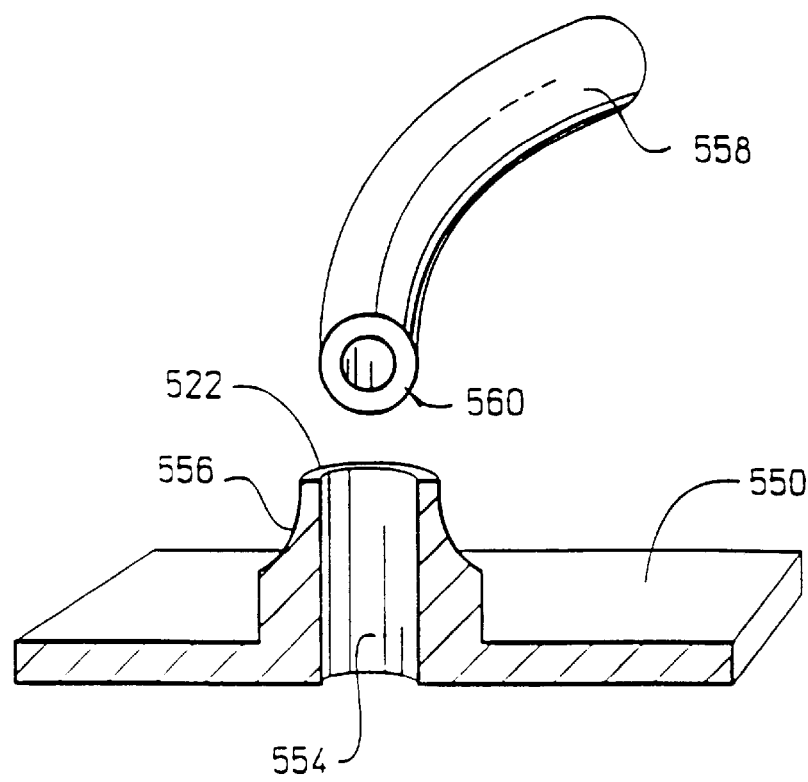
FIG. 21 is a pictorial representation of a keeper means having an annular boss that is adapted to cooperate with an associated conduit or lightguide means.

By providing annular bosses that have an inner diameter constructed within close tolerances, associated lightguide means or conduit means can be butt-coupled to the periphery of the column device 522 and frictionally held in place to provide a liquid-tight seal. Referring to FIG. 21, an opposable element 550 of a keeper means is depicted as having an annular boss 552 in the form of a projecting cylinder. The cylinder has an interior and an exterior surface, respectively indicated at 554 and 556. A distal terminus, 560, of an associated conduit means 558 can be inserted into the annular boss 552 and held in place as has been described above.

A keeper means may also be configured to have an optional lock means for detachably coupling a fastener, such as a conduit means or lightguide means, with an aperture, inlet, outlet or detection means on a miniaturized column. Referring to FIG. 20, the annular boss 536 is configured to cooperate with a closure 572. The closure comprises a sleeve that is disposed about the lightguide means 540. In practice, after the distal end 542 of the lightguide has been inserted into the annular boss, the closure 572 is slidably positioned about the periphery of the boss to provide a locking snap-fit in cooperation with the exterior surface of the annular boss 536.

The optional lock means can comprise machined threads arranged on the outer surface of an annular boss for threadably engaging mating threads arranged on the interior of a closure, such as a cap or the sleeve 572 depicted in FIG. 20. The threads enable an associated conduit means or lightguide means to be coupled to a miniaturized column device disposed within a keeper, and then locked into place to provide a superior liquid-tight seal.

Figure 22:
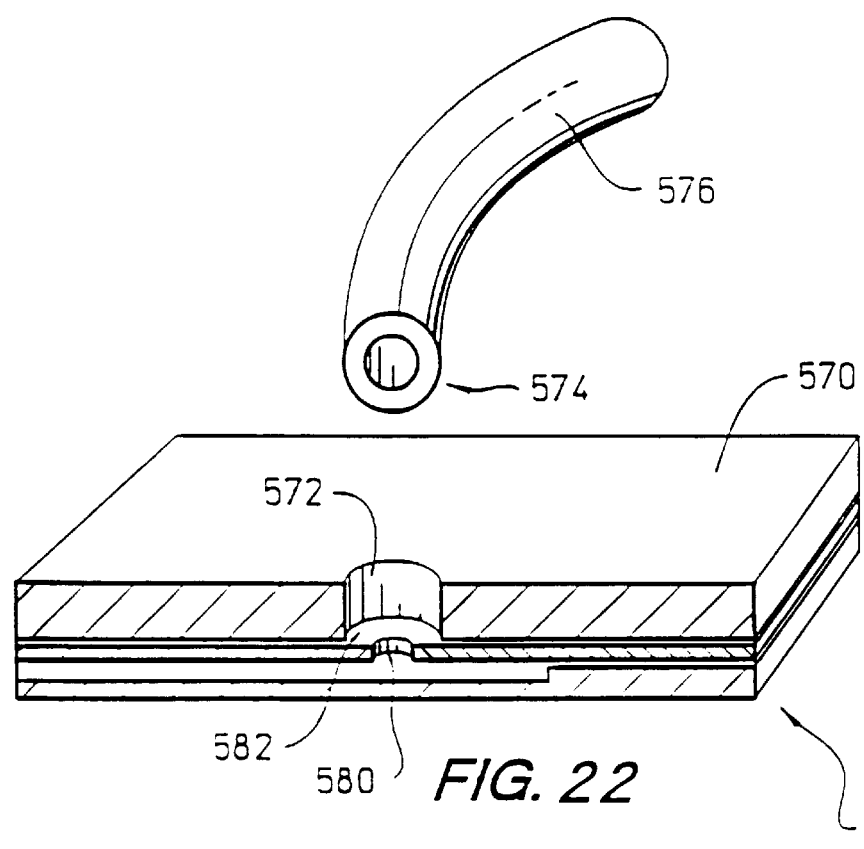
FIG. 22 is a pictorial representation of a keeper means having an aperture that is adapted to cooperate with an associated conduit or lightguide means.

An alternative keeper means may be provided having one or more apertures that facilitate the coupling of a fastener with an inlet port, outlet port, aperture or detection means in a miniaturized column. Referring now to FIG. 22, an opposable element 570 of a keeper means having an aperture 572 formed therein is depicted. The aperture is arranged in the keeper such that it encompasses an inlet port, aperture, detection means, or a like feature of a miniaturized column 578 that is disposed within the keeper. The distal end 574 of an associated conduit means 576 can be inserted into the aperture 572 and butt-coupled to the column device 578. Thus the aperture 572 can be sized to closely cooperate with the inserted conduit to resiliently maintain the coupling of the conduit to the column device, and to provide a liquid-tight seal.

In one particular configuration, the keeper aperture 572 is sized to have a greater diameter than that of the coaxially arranged column inlet port, outlet port or detection means. Referring still to FIG. 22, the keeper aperture 572 encompasses an aperture 580 in the miniaturized column device 578 that is disposed within the keeper means. The aperture 580 has a smaller diameter than that of the aperture 572. In this manner, a shoulder 582 is provided that serves as a sealing stop surface that cooperates with the distal end 574 of the inserted conduit means 576 to provide a liquid-tight seal. This particular configuration allows the conduit means to be urged to couple closely with the surface of the column device and provide a resilient liquid-tight seal, without the possibility of having the conduit means travel into the column device where it could interfere with the flow of liquids passing through the column device.

Accordingly, a number of liquid phase separation apparatus configurations have been described. It is to be understood that while the various elements of such configurations, such as the manifolds and rotors, keepers means, associated lightguide means and conduit means, have been described individually, it is expressly intended herein to combine such elements to provide a wide variety of apparatus configurations. Thus, keeper means used in the practice of the invention can be configured to cooperate with various manifold configurations, micropumps, actuators, and the like.

Figure 23:
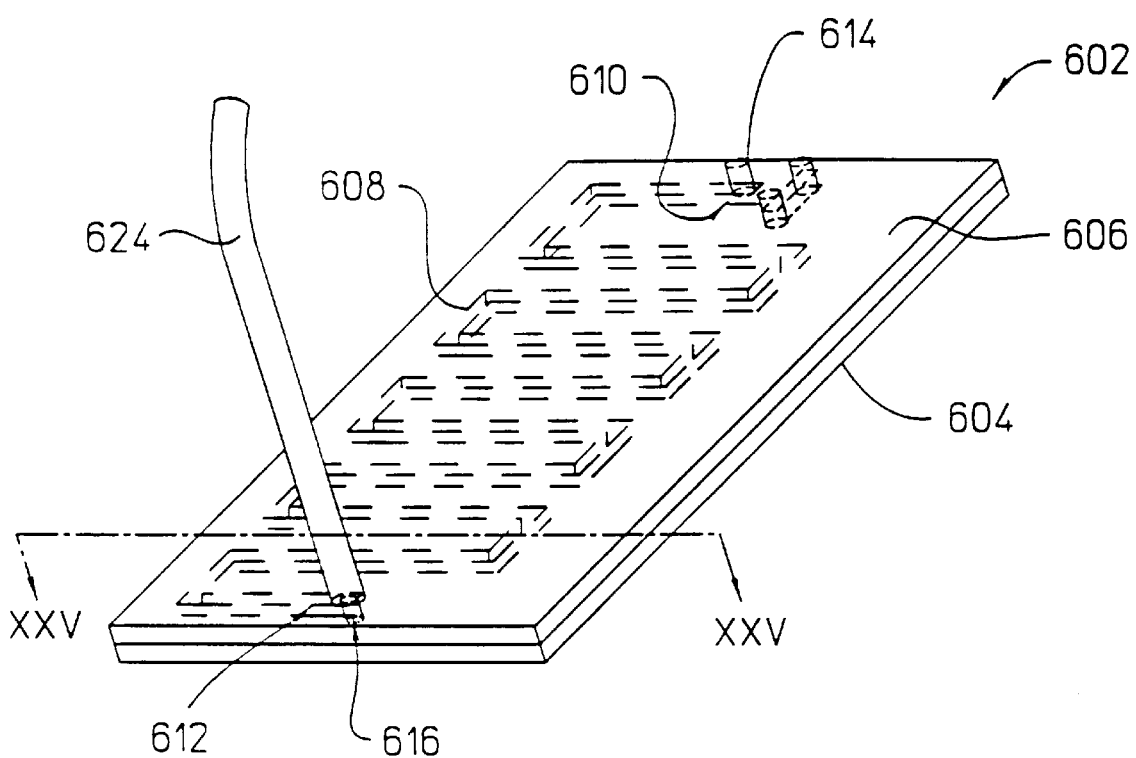
FIG. 23 is pictorial representation of an optional means for generating and expelling a sample eluate droplet from a liquid phase separation apparatus.
Figure 24:
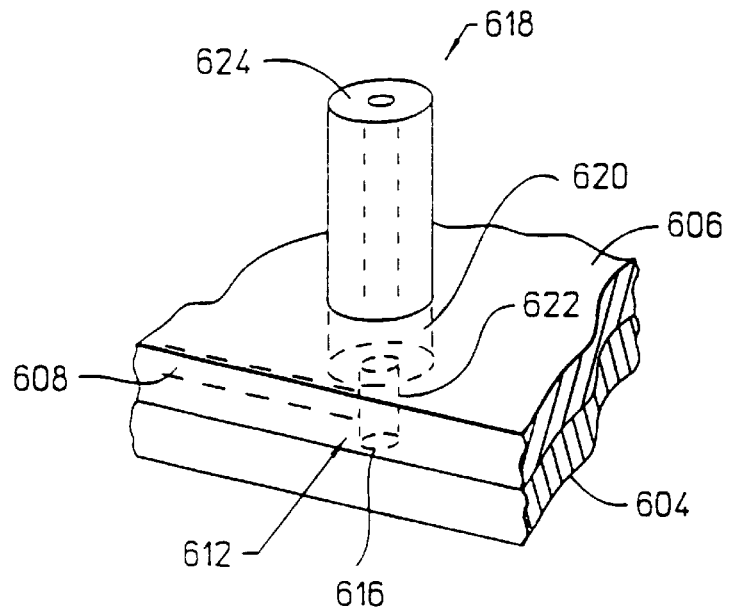
FIG. 24 is a pictorial representation of the interface of the means for generating and expelling a sample eluate droplet and the apparatus.
Figure 25:
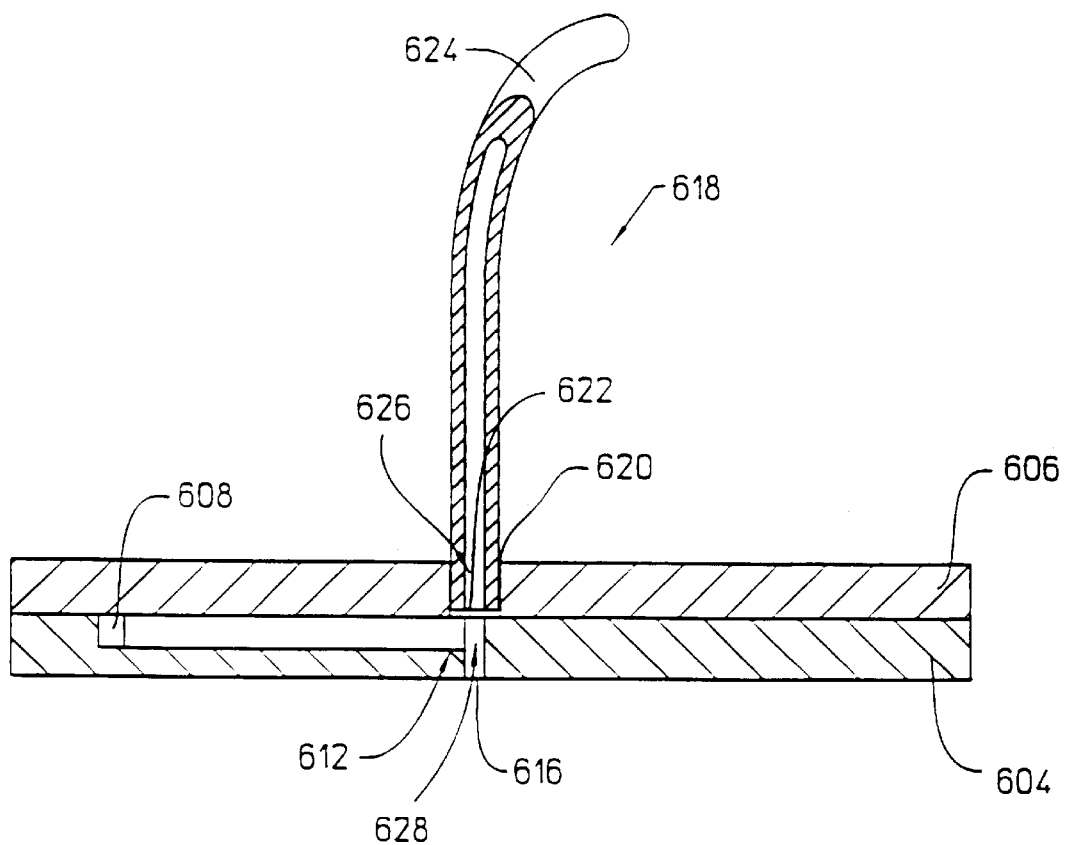
FIG. 25 is a cross-sectional view of the means for generating and expelling a sample eluate droplet of FIG. 23 taken along lines XXV—XXV.
Figure 26A:
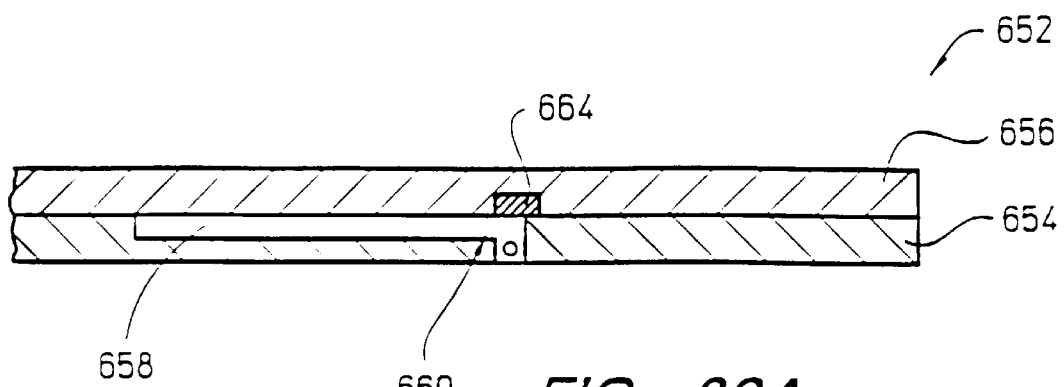
FIGS. 26A–26D are pictorial representations in cross section that depict the generation and expulsion of a sample eluate droplet from a liquid phase separation apparatus.
Figure 26B:
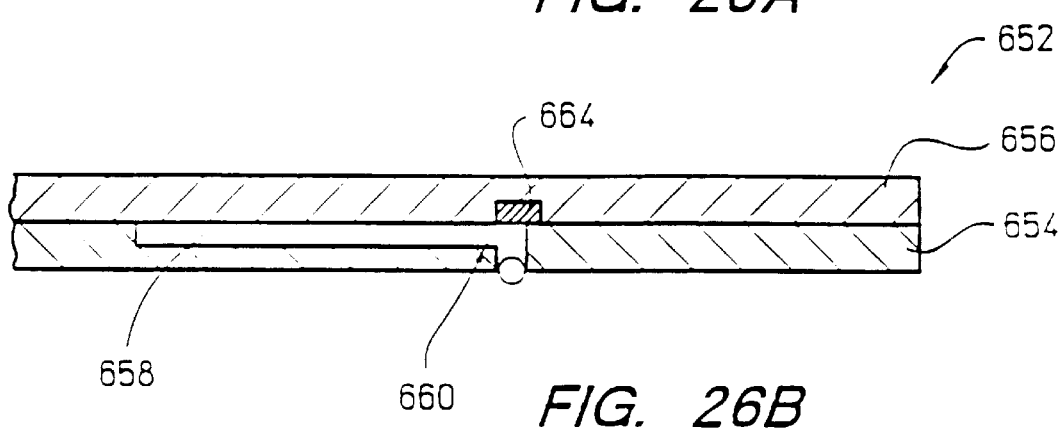
Figure 26C:
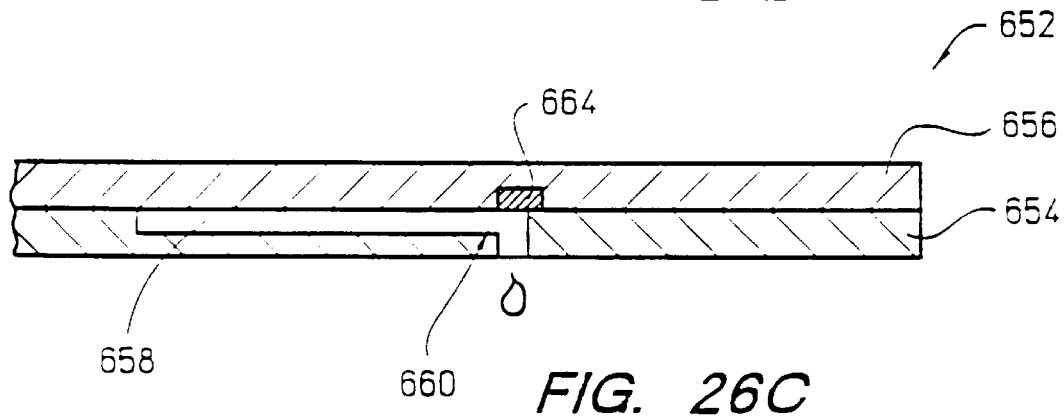
Figure 26D:
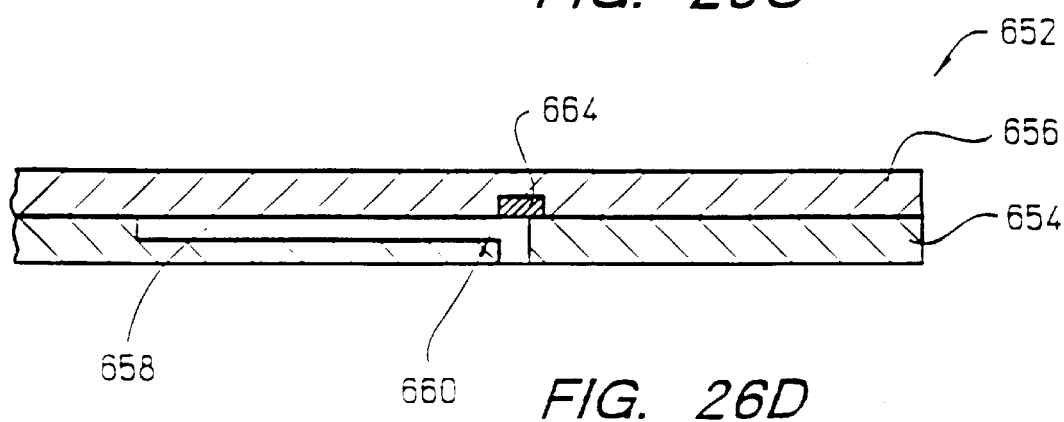

In yet a further embodiment of the invention, a liquid phase separation apparatus is provided having means for assisting in the generation and expulsion of a sample eluate droplet from the separation compartment of a miniaturized column device. Referring to FIGS. 23–25, a miniaturized column 602 is shown that is formed from a substrate portion 604 and a cover plate portion 606 as has been described above. The column includes a separation compartment 608 having an upstream terminus 610 and a downstream terminus 612. An inlet port 614 is provided, and generally comprises an aperture arranged in the cover plate 606 to be in fluid communication with the upstream terminus 610 of the separation compartment when the cover plate is affixed above the substrate portion 604. An outlet port 616 is also provided, comprising an aperture formed in the substrate portion 604 that is in fluid communication with the downstream terminus 612 of the separation compartment. A flow path is formed that extends from the upstream terminus and travels along the length of the separation compartment to the downstream terminus. A liquid medium or sample housed in an associated containment means can be delivered to the upstream terminus 610 of the separation compartment by communicating a conduit from the containment means with the inlet port 614 via a manifold means or with the assistance of a keeper means as described above.

Referring still to FIGS. 23–25, the column device 602 also includes a sample eluate delivery means, generally indicated at 618, that is arranged adjacent to the downstream terminus 612 of the separation compartment. Specifically, the eluate delivery means 618 includes a recess 620 formed in the cover plate 606. An aperture 622 is disposed within the recess 620 and is arranged to be coaxially aligned and in fluid communication with the outlet port 616. The delivery means also includes an associated conduit means 624, wherein the distal end 626 is inserted into the recess 620 and butt-coupled to the aperture 622. An eluate from the separation compartment can be expelled from the outlet port by communicating an external pulsed air stream with the conduit means 624 to urge small fractions from the column by air pressure pulses, which fractions may then be collected using known techniques.

The conduit means can alternatively be interfaced with an external source of makeup fluids, enabling the communication of such fluids via the conduit means, through the aperture 622 and into contact with sample eluate emitting into the outlet port 616 from the downstream terminus 612 of the separation compartment 608. Referring to FIG. 25, this particular configuration provides a mixing chamber 628 which is formed from the intersection of the downstream terminus 612 of the separation compartment, the aperture 622 (which comprises a mixing chamber inlet means), and the outlet port 616. The outlet port 616 may optionally be tapered to provide an outlet nozzle. Droplets, containing a mixture of sample eluate and makeup fluid, are generated and expelled from the mixing chamber and may be collected using known techniques.

An alternative means for generating and expelling a sample eluate droplet from a miniaturized column device is shown in FIGS. 26A–26D. Specifically, a miniaturized column is indicated at 652. The column is formed from a substrate portion 654 and a cover plate portion 656, and includes a separation compartment 658 having a downstream terminus 660 in fluid communication with a sample delivery means 662, comprising an outlet port. A heating means 664 disposed within the cover plate 656 is arranged in thermal contact with the sample delivery means. By actuating the heating means, the temperature in the sample delivery means is increased. As the temperature increases, a steam bubble builds up in the sample delivery means 662, thereby forming sample droplet 668 which is expelled from the column device. For further discussion of fluid delivery using this method see Allen et al. (1985) *Hewlett3-Packard J.* May 1985:21–27.

Figure 27:
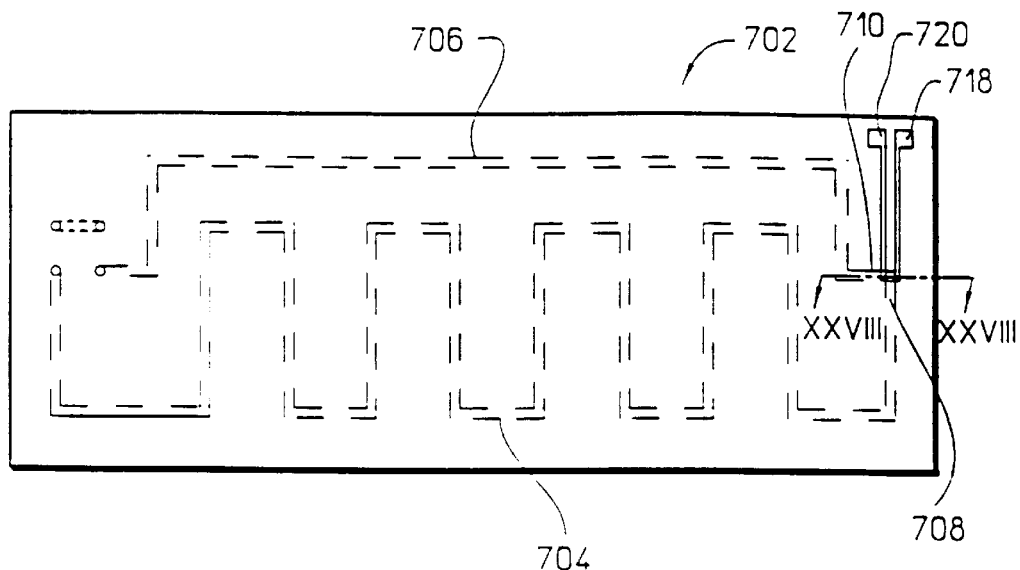
FIG. 27 is a plan view of a liquid phase separation apparatus having an alternative means for generating and expelling a sample eluate droplet that is actuated via electrical contacts.
Figure 28:
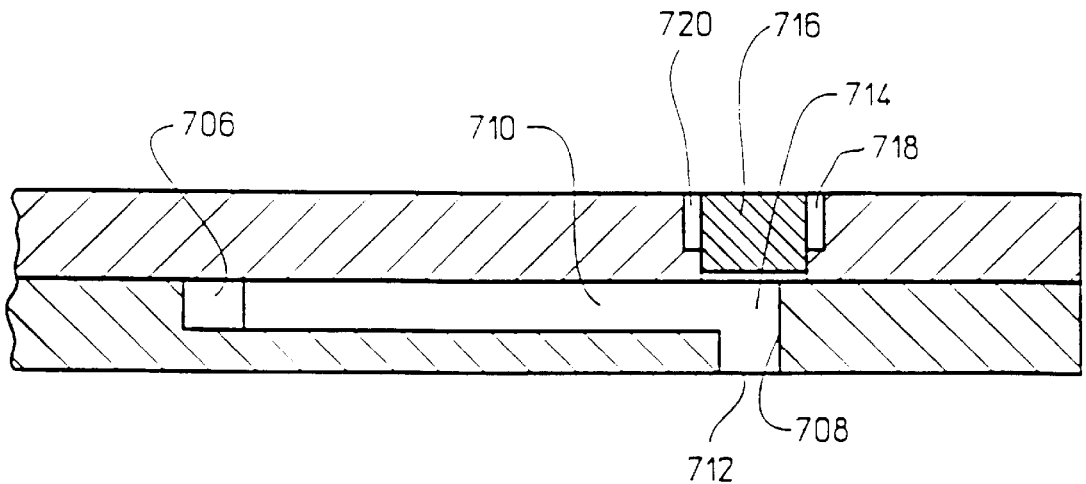
FIG. 28 is a cross-sectional representation of the apparatus of FIG. 27 taken along lines XXVIII–XXVIII.

Yet another alternative means for generating and expelling a sample eluate droplet from a miniaturized column device is shown in FIGS. 27 and 28. As best seen in FIG. 27, a miniaturized column device 702 is provided having a separation compartment 704 and a makeup flow compartment 706 comprising channels that have been laser-ablated in the surface of a suitable planar substrate. Referring now to FIGS. 27 and 28, the separation compartment and the makeup flow compartment converge with a sample outlet nozzle 712 at their respective downstream termini, 708 and 710, to form a mixing chamber 714 wherein sample eluate exiting from the separation compartment 704 can intermix with makeup fluid exiting from the makeup flow compartment 706. A heating means 716 is situated in thermal contact with the mixing chamber 714. As described above, actuation of the heating means 716 results in the increase in the temperature thereof, the build up of a steam bubble in the mixing chamber 714, and the formation and expulsion of a sample eluate droplet. In one particular configuration, the heating means comprises a resistor type heating element that is actuated via first and second electrical contacts 718 and 720 using an associated source of electrical power.

Figure 29:
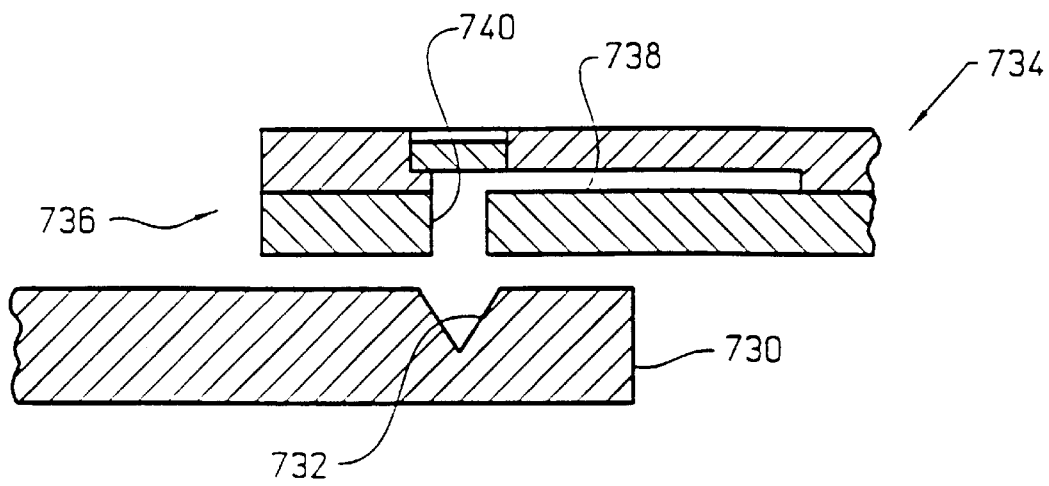
FIG. 29 is a pictorial representation in cross section of optional means for collecting a sample eluate droplet from a miniaturized column device or liquid phase separation apparatus.

In each of the above-described embodiments, an optional post-column collection means can be positioned relative to an outlet port or outlet nozzle to collect sample eluate exiting from the separation compartment. Referring to FIG. 29, a post-column collection device 730 (shown in cross-section) may be a substrate in which sample eluate droplet receiving microwell 732 has been laser-ablated. As described with respect to other microstructures formed by laser ablation, microwell 732 may be of any geometry and any aspect ratio.

Figure 30:
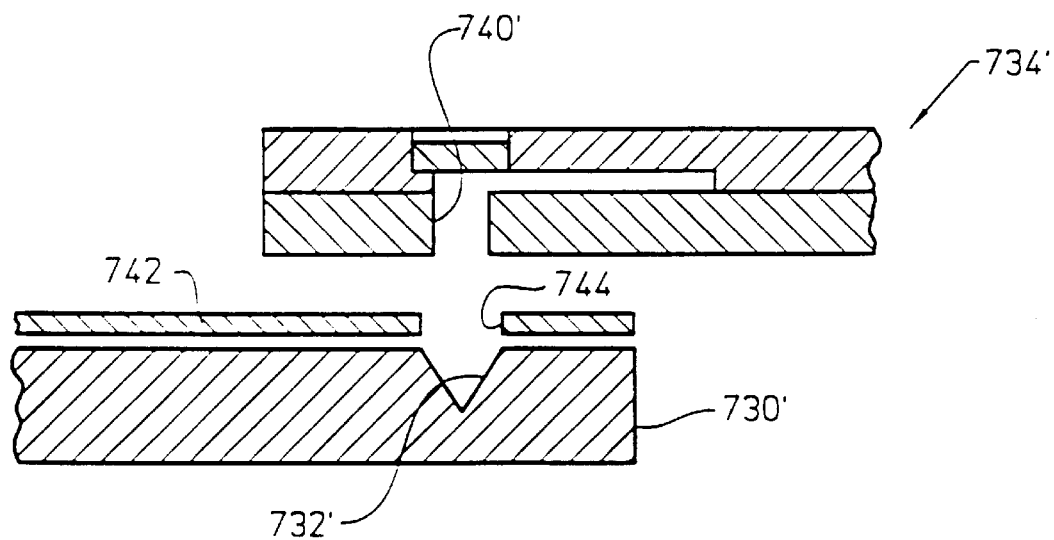
FIG. 30 is a pictorial representation in cross section of an alternative means for collecting a sample eluate droplet from a miniaturized column device or liquid phase separation apparatus.

More specifically, the collection device 730 is positioned relative to the distal end 736 of a miniaturized column device 734 such that sample eluate drops emanating from a separation compartment 738 and passing through an outlet port 740 can be collected for post-separation analysis or for further manipulations. Referring now to FIG. 30, a post-column collection device 730' (also shown in cross-section) may be a substrate in which sample droplet receiving microwell 732' has been laser-ablated. In addition, protective plate 742 can be removably interposed between the column device 734' and the post-column collection device 730'. The protective plate 742 generally comprises a structure having an opening 744 that is arranged to be in axial alignment with the outlet port 740' and receiving well 732' and is intended to provide protection of empty or filled wells from contamination or from evaporation of sample droplets previously collected.

Figure 31:
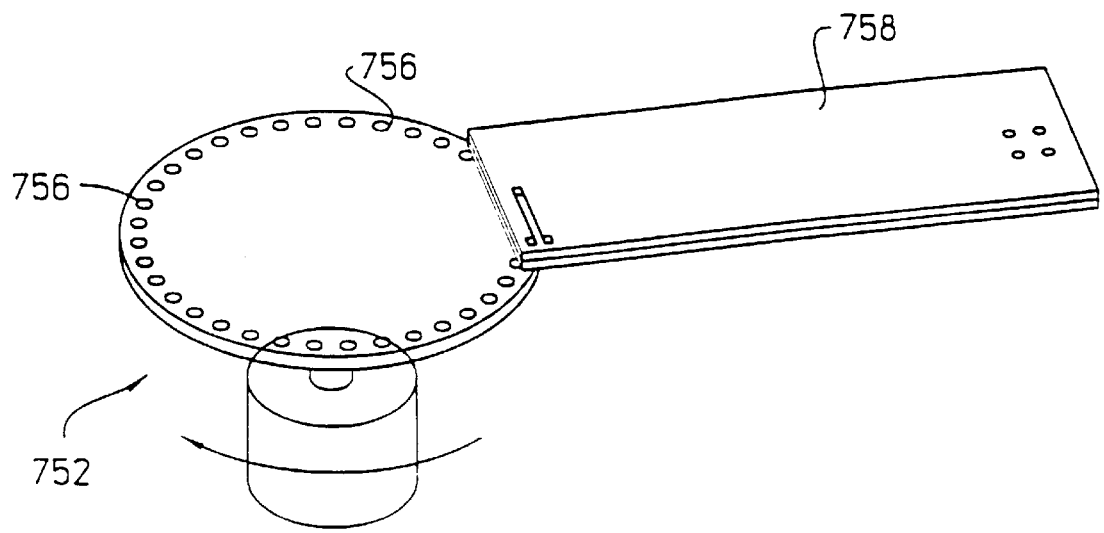
FIG. 31 is a pictorial representation of an alternative means for collecting a sample eluate droplet from a miniaturized column device or liquid phase separation apparatus, wherein the sample collection means is rotatable relative to the device or apparatus.
Figure 32:
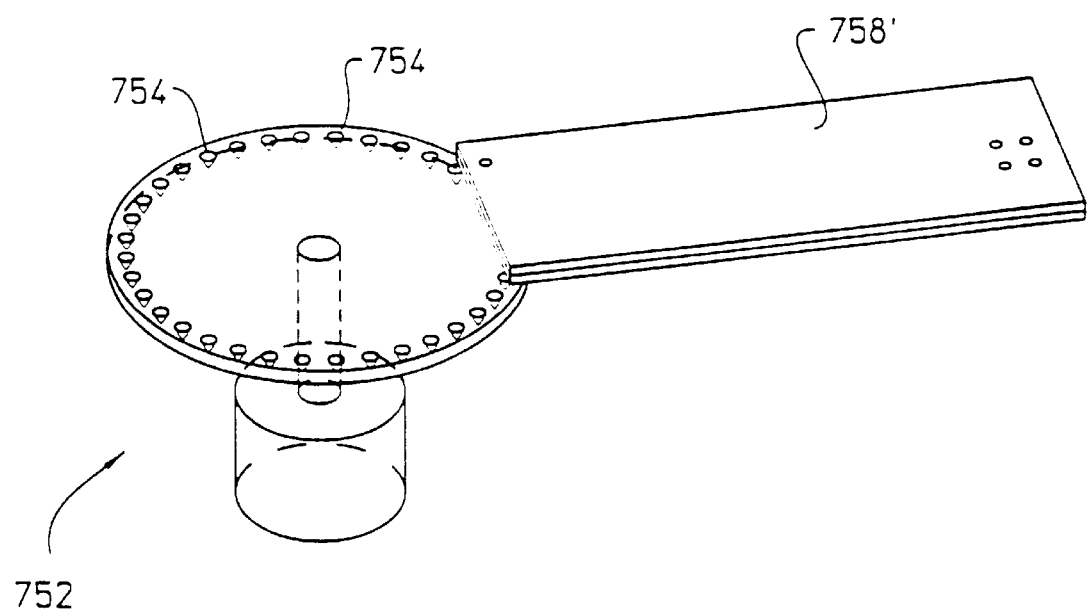
FIG. 32 is a pictorial representation of the sample collection means of FIG. 31 comprising optional sample collection microwells.

Referring now to FIGS. 31 and 32, a post-column collection device 752 comprising sample receiving means that may be sample receiving wells 754 or bibulous sheet means 756 is positioned relative to the outlet port of a miniaturized column device 758 or 758' to receive sample eluate droplets emitted from the column. Referring to FIG. 32, the sample receiving means can preferably be one or more microwells 754 laser-ablated in a substrate for liquid phase sample collection. Alternatively, the sample receiving means can be one or more bibulous sheet means 756 for solid-phase sample collection as shown in FIG. 31. The substrate used in the construction of the post-column collection device 752 is optionally a material other than silicon or silicon dioxide wherein microwells 754 can be laser-ablated in the substrate.

As shown in FIGS. 31 and 32, the receiving means can preferably be in rotatable alignment with the outlet port of the miniaturized column 758 or 758' such that multiple fractions may be collected. Further, as described above, the post-column collection device 752 can include a protection means having an opening that is arranged to be in axial alignment with the outlet port of the column device, wherein the protection means is interposed between the miniaturized column 758 or 758' and the sample receiving means. Although the post-column collection device 752 has been depicted herein as a disc in rotatable alignment with column device 758, it will be recognized by one of skill in the art that the configuration of the collection device need not be so limited. Thus, the post-column collection device 752 may be configured, for example, as a linear arrangement of sample receiving wells 754, or the like.

Further, while the present invention has been described with reference to specific preferred embodiments, it is understood that the description and examples included herein are intended to illustrate and not limit the scope of the invention, which is defined by the scope of the appended claims.

We claim:

1. A miniaturized column device comprising:

a substrate having a first substantially planar surface, wherein said substrate is comprised of a material other than silicon or silicon dioxide;

a separation channel comprising a microchannel laser-ablated in the first planar surface;

reservoir means comprising a cavity laser-ablated in the first planar surface;

fluid conducting means comprising a duct laser-ablated in the first planar surface enabling fluid communication between the separation channel and the reservoir means;

a bypass microchannel laser-ablated in the first planar surface that is distinct from and unconnected to the separation channel and the reservoir means;

a first cover plate arranged over the first planar surface that respectively defines a separation compartment in combination with the separation channel, a reservoir compartment in combination with the reservoir means, a fluid conducting compartment in combination with the fluid conducting means, and a volumetric sample compartment in combination with the bypass microchannel; and an inlet port and at an outlet port communicating with the separation compartment, said ports enabling passage of fluid from an external source through the separation compartment.

2. The miniaturized column of claim 1, wherein the cover plate comprises an orifice enabling the passage of fluid from an external source into the reservoir compartment.

3. The miniaturized column of claim 1, further comprising first detection means in communication with the separation compartment thereby enabling detection of a sample passing through the separation compartment.

4. The miniaturized column of claim 1, further comprising motive means enabling the displacement of fluid from the reservoir compartment through the fluid conducting compartment and into the separation compartment.

5. A miniaturized column device comprising:
   a substrate having a first substantially planar surface, wherein said substrate is comprised of a material other than silicon or silicon dioxide;
   a separation channel comprising a microchannel laser-ablated in the first planar surface, wherein said separation channel has an upstream and a downstream terminus; and
   a makeup flow channel extending substantially along the length of the separation channel, comprising a duct laser-ablated in the first planar surface and having an upstream terminus and a downstream terminus, wherein the downstream terminus of the makeup flow channel is in communication with the downstream terminus of the separation channel;
   a first cover plate arranged over the first planar surface that respectively defines a separation compartment in combination with the separation channel, and a makeup flow compartment in combination with the makeup flow channel; and
   an inlet port in communication with the upstream terminus of the separation channel, an outlet port in communication with the downstream terminus of the separation compartment, said ports enabling passage of fluid from an external source through the separation compartment, and a makeup compartment inlet in communication with the upstream terminus of the makeup flow channel.

6. The miniaturized column of claim 5, further comprising first detection means in communication with the separation compartment thereby enabling detection of a sample passing through the separation compartment.

7. The miniaturized column of claim 5, wherein said cover plate comprises an aperture positioned so as to allow passage of a makeup fluid stream into the upstream terminus of the makeup flow channel.

8. A liquid phase separation apparatus comprising:
   (a) a miniaturized column, comprising (i) a substrate having a first substantially planar surface, wherein said substrate is comprised of a material other than silicon or silicon dioxide, (ii) a separation channel comprising a microchannel laser-ablated in the first planar surface, (iii) a first cover plate arranged over the first planar surface, whereby said cover plate defines a separation compartment in combination with the separation channel, and (iv) at least one inlet port and at least one outlet port communicating with the separation compartment, said ports enabling the passage of fluid from an external source through the separation compartment;
   (b) associated containment means for housing a sample to be separated;
   (c) injection means for introducing the sample into the column from the associated containment means;
   (d) means for applying a motive force along the column such that the sample is moved therethrough; and
   (e) detecting means for detecting separated analytes of interest contained in the sample.

9. The liquid phase separation apparatus of claim 8, wherein the injection means comprises a manifold having a volumetric sample compartment formed therein, said manifold arranged in divertable fluid communication with the inlet port and the associated containment means.

10. The liquid phase separation apparatus of claim 8, further comprising an associated keeper means having first and second opposable elements and adapted for receiving the miniaturized column device.

11. The liquid phase separation apparatus of claim 10, wherein the keeper means is further adapted to provide a means for facilitating the coupling of a fastener with the inlet port, outlet port or detection means.

12. The liquid phase separation apparatus of claim 11, wherein the keeper means comprises at least one annular boss arranged to encompass an inlet port, outlet port or detection means.

13. The liquid phase separation apparatus of claim 12, wherein the annular boss comprises a cylinder having an interior and an exterior surface.

14. The liquid phase separation apparatus of claim 13, wherein the annular boss further comprises lock means for detachably coupling a fastener with the inlet port, outlet port or detection means.

15. The liquid phase separation apparatus of claim 14, wherein the lock means comprises thread means arranged on the exterior surface of the annular boss for threadably engaging a fastener.

16. The liquid phase separation apparatus of claim 12, wherein the annular boss is configured to facilitate interfacing of an associated lightguide means with the detection means.

17. The liquid phase separation apparatus of claim 11, wherein the keeper, means comprises at least one aperture arranged to be in coaxial relation with an inlet port, outlet port or detection means when a miniaturized column device is disposed within the keeper means.

18. The liquid phase separation apparatus of claim 17, wherein the aperture has a greater diameter than that of the coaxially arranged inlet port, outlet port or detection means.

19. The liquid phase separation apparatus of claim 8, wherein the miniaturized column inlet port and outlet port enable the formation of a sample eluent within the separation compartment, said separation apparatus further comprising:
   (a) sample eluate delivery means comprising a mixing chamber, wherein the mixing chamber includes a first side in fluid communication with the outlet port, a top end in fluid communication with a mixing chamber inlet means, and a bottom end in fluid communication with an outlet nozzle;

(b) a fluid source in divertable fluid communication with the mixing chamber inlet means; and (c) a post-column collection device comprising a sample eluate receiving means positioned relative to the outlet nozzle, thereby enabling the collection of the sample eluate.

20. The liquid phase separation apparatus of claim 19, further comprising a means for heating the fluid source.

21. The liquid phase separation apparatus of claim 19, further comprising protection means interposed between the miniaturized column device and the sample eluate receiving means, said protection means comprising an opening arranged in axial alignment with the outlet nozzle.

22. A liquid phase separation apparatus comprising:

(a) a miniaturized column, comprising (i) a substrate having a first substantially planar surface, wherein said substrate is comprised of a material other than silicon or silicon dioxide, (ii) a separation channel comprising a microchannel laser-ablated in the first planar surface, (iii) a first cover plate arranged over the first planar surface, whereby said cover plate defines a separation compartment in combination with the separation channel, (iv) at least one inlet port and at least one outlet port communicating with the separation compartment, said ports enabling the passage of fluid from an external source through the separation compartment, and (v) a bypass microchannel laser-ablated in the first planar surface, wherein the first cover plate in combination with the bypass microchannel defines a volumetric sample compartment having first and second ends;

(b) associated containment means for housing a sample to be separated; and (c) injection means for introducing the sample into the column from the associated containment means, comprising a manifold in fluid communication with the containment means and in divertable fluid communication with the volumetric sample compartment and the inlet port.

23. The liquid phase separation apparatus of claim 22, wherein the manifold is further in fluid communication with a second associated containment means housing a liquid medium.

24. The liquid phase separation apparatus of claim 22, wherein the manifold is movable between a plurality of positions relative to the miniaturized column device.

25. The liquid phase separation apparatus of claim 24, wherein the manifold is movable between a first and a second position, whereby the manifold in said first position enables dynamic fluid communication between the volumetric sample compartment and the associated containment means to allow a sample plug to be formed by the passage of sample through the volumetric sample compartment, said plug corresponding to the dimensions of the sample compartment, and further whereby the manifold in said second position allows movement of the sample plug from the sample compartment to the separation compartment.

26. The liquid phase separation apparatus of claim 24, wherein the manifold comprises a rotor detachably coupled to the miniaturized column device.

27. The liquid phase separation apparatus of claim 21, wherein the manifold comprises an elongated housing detachably coupled to the miniaturized column device.

28. The liquid phase separation apparatus of claim 22, wherein the miniaturized column inlet port and outlet port enable the formation of a sample eluent within the separation compartment, said separation apparatus further comprising:

(a) sample eluate delivery means comprising a mixing chamber, wherein the mixing chamber includes a first side in fluid communication with the outlet port, a top end in fluid communication with a mixing chamber inlet means, and a bottom end in fluid communication with an outlet nozzle;

(b) a fluid source in divertable fluid communication with the mixing chamber inlet means, and (c) a post-column collection device comprising a sample eluate receiving means positioned relative to the outlet nozzle, thereby enabling the collection of the sample eluate.

29. The liquid phase separation apparatus of claim 28, further comprising a means for heating the fluid source.

30. The liquid phase separation apparatus of claim 28, further comprising protection means interposed between the miniaturized column device and the sample eluate receiving means, said protection means comprising an opening arranged in axial alignment with the outlet nozzle.

* * * * *